US009888902B2

(12) United States Patent
Ueki et al.

(10) Patent No.: US 9,888,902 B2
(45) Date of Patent: Feb. 13, 2018

(54) X-RAY CT DEVICE, CALCURATION DEVICE, RECORDING MEDIUM FOR X-RAY CT DEVICE, AND MAINTENANCE METHOD FOR X-RAY CT DEVICE

(75) Inventors: Hironori Ueki, Tokyo (JP); Fumito Watanabe, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 1069 days.

(21) Appl. No.: 14/131,917

(22) PCT Filed: Jul. 5, 2012

(86) PCT No.: PCT/JP2012/067186
§ 371 (c)(1),
(2), (4) Date: May 20, 2014

(87) PCT Pub. No.: WO2013/008712
PCT Pub. Date: Jan. 17, 2013

(65) Prior Publication Data
US 2014/0321608 A1      Oct. 30, 2014

(30) Foreign Application Priority Data

Jul. 12, 2011  (JP) .................. 2011-153981

(51) Int. Cl.
*A61B 6/00* (2006.01)
*A61B 6/03* (2006.01)
*G06T 11/00* (2006.01)

(52) U.S. Cl.
CPC .............. *A61B 6/583* (2013.01); *A61B 6/032* (2013.01); *A61B 6/5258* (2013.01); *G06T 11/005* (2013.01); *G06T 2207/10081* (2013.01)

(58) Field of Classification Search
CPC ................ A61B 6/032; A61B 6/5258; G06T 2207/10081; G06T 11/005
See application file for complete search history.

(56) References Cited

U.S. PATENT DOCUMENTS

2004/0109528 A1   6/2004  Nukui et al.
2006/0203956 A1   9/2006  Raupach
(Continued)

FOREIGN PATENT DOCUMENTS

AT        408159 T      9/2008
BR        7900096 A     8/1979
(Continued)

OTHER PUBLICATIONS

International Search Report issued in corresponding application No. PCT/JP2012/067186 dated Sep. 4, 2012. International Publication issued in corresponding application No. PCT/JP2012/067186 dated Jan. 17, 2013.
International Preliminary Report on Patentability in corresponding application No. PCT/JP2012/067186 dated Jan. 14, 2014.

*Primary Examiner* — Dani Fox
(74) *Attorney, Agent, or Firm* — Brundidge & Stanger, P.C.

(57) ABSTRACT

In X-ray CT devices, degradation of quantitative determination ability for CT values resulting from the beam hardening (BH) effect of X-ray is prevented. X-ray absorption characteristic S obtained by simulation and a target value T thereof are saved beforehand, the simulation value S is revised by using projection data measured by maintenance measurement for obtaining basic data required for BH correction, and a BH correction coefficient is calculated by using the revised X-ray absorption characteristic S and the target value T. With a few actually measured values, BH correction accuracy can be improved, and reduction of incorrect diagnosis resulting from inhomogeneity of the CT values and improvement in the diagnostic ability based on improvement in quantitative determination ability for the CT values can be realized.

18 Claims, 15 Drawing Sheets

(56) References Cited

U.S. PATENT DOCUMENTS

| | | | |
|---|---|---|---|
| 2007/0092056 A1* | 4/2007 | Flohr | A61B 6/032 378/4 |
| 2007/0116183 A1* | 5/2007 | Ueki | A61B 6/5258 378/207 |
| 2008/0317320 A1 | 12/2008 | Van Stevendaal et al. | |

FOREIGN PATENT DOCUMENTS

| | | |
|---|---|---|
| CN | 1504169 A | 6/2004 |
| CN | 1823685 A | 8/2006 |
| DE | 2800761 A | 7/1979 |
| DE | 102005008767 A | 9/2006 |
| DE | 602004016560 D | 10/2008 |
| EP | 1700137 A1 | 9/2006 |
| FR | 2414206 A | 7/1979 |
| GB | 2012516 A | 7/1979 |
| JP | 54-110888 A | 8/1979 |
| JP | 61-054412 B | 3/1986 |
| JP | 05-130987 A | 5/1993 |
| JP | 2004178247 | 6/2004 |
| JP | 2004-180808 A | 7/2004 |
| JP | 2006075387 | 3/2006 |
| JP | 2006-231058 A | 9/2006 |
| JP | 2006-334319 A | 12/2006 |
| JP | 2007-513725 A | 5/2007 |
| KR | 10-2004-0048362 A | 6/2004 |
| NL | 7900044 A | 7/1979 |
| SE | 7900109 A | 7/1979 |
| WO | 2005-059592 A1 | 6/2005 |

\* cited by examiner

X-RAY CT DEVICE, CALCURATION DEVICE, RECORDING MEDIUM FOR X-RAY CT DEVICE, AND MAINTENANCE METHOD FOR X-RAY CT DEVICE

TECHNICAL FIELD

The present invention relates to a method for correcting degradation of homogeneity of CT images caused by the beam hardening effect of X-rays in an X-ray CT device.

BACKGROUND ART

X-ray CT devices are devices for reconstructing a tomographic image (henceforth referred to as CT image) of a subject by using transmission X-ray data of the subject obtained by imaging the subject with revolving a pair of X-ray tube and X-ray detector oppositely disposed on both sides of the subject (henceforth referred to as imaging system), and they are widely used in the field of diagnostic imaging. It is well known that since X-rays emitted from X-ray tubes are usually polychromatic X-rays, there is induced the beam hardening (henceforth abbreviated as BH) phenomenon. The BH phenomenon is a phenomenon that energy of an X-ray passing through a subject and detected by an X-ray detector becomes higher as X-ray transmission path length of the X-ray in the subject becomes longer. The BH phenomenon is a cause of reduction of quantitative determination ability for CT values in CT images and homogeneity of the same as explained below.

FIG. 20 shows the relation between transmission path length L of X-ray passing through a subject consisting of a uniform material and having uniform density and a projection data p (henceforth referred to as X-ray absorption characteristic). In this case, the values of the projection data p are values corrected by the known air correction.

As shown in FIG. 20, when the X-ray is a monochromatic X-ray, the X-ray absorption characteristic is represented by a straight line $p_o = \mu_o L$, which means that the projection data $p_o$ corrected by the air correction is proportional to the X-ray transmission path length L. In the equation, $\mu_o$ is the X-ray absorption coefficient of the subject for the aforementioned monochromatic X-ray. In contrast, when the X-ray is a polychromatic X-ray, the energy of the X-ray detected by the X-ray detector becomes higher due to the influence of the BH phenomenon as the X-ray transmission path length L becomes longer, and therefore average X-ray absorption coefficient of the subject decreases. As a result, as shown in FIG. 20, the X-ray absorption characteristic for the X-ray transmission path length L is represented by the curve $p_m$. A CT image obtained by reconstruction of projection data represents spatial distribution of the X-ray absorption coefficient $\mu_0$ of a subject. Therefore, a CT image of such a subject consisting of a uniform material and having uniform density as mentioned above should naturally have uniform CT values. However, in fact, there arises a problem that the density of the CT image changes depending on the position in the CT image due to the influence of the BH effect.

There is well known a BH correction method for preventing reduction of accuracy of the CT value due to the BH effect, in which projection data are corrected in advance of the reconstruction operation. In the BH correction, projection data of a polychromatic X-ray are corrected by using a function representing the relation between projection data $p_m$ of a polychromatic X-ray and projection data $p_o$ of a monochromatic X-ray (henceforth this function is referred to as BH correction function). The BH correction function is such a function $A(p_m)$ as shown in FIG. 21, and is generally approximated with such a polynomial as represented by the following equation (1), and the coefficients of the polynomial (henceforth referred to as BH correction coefficients) are used for the BH correction.

[Equation 1]

$$p_o = A(p_m) = a_1 p_m + a_2 p_m^2 + \ldots + a_K p_m^K \quad (1)$$

As the method for calculating the BH correction coefficients, there are methods of calculating them by using a phantom or by simulation, and Patent documents 1 and 2 propose methods of using a phantom.

For example, according to the method disclosed in Patent document 1, the measurement is performed by using a phantom having a cylindrical shape and formed with a polyethylene material having uniform density to obtain projection data measured with detection elements (data corrected by the air correction). By performing the same measurement for a plurality of phantoms having different diameters, a plurality of sets of projection data can be obtained for different X-ray transmission path lengths (lengths of the phantoms through which a beam passes). By performing least square fitting of these data on the polynomial of the equation (1), the X-ray absorption characteristic can be obtained. Further, the theoretical value of the X-ray absorption characteristic of a phantom having a uniform density is proportional to the X-ray transmission path length ($p_o = \mu_o L$), and can be obtained by calculation, and therefore the BH correction function and the correction coefficients are calculated by using this theoretical value and measured X-ray absorption characteristic.

In the method described in Patent document 2, a water phantom is used as the phantom. The water phantom WP consists of a cylindrical container formed with such a material as an acrylic resin the inside of which is filled with water. In X-ray CT devices for medical use, it is necessary to optimize the BH correction for the human body, which is the object of imaging. It is known that 60 to 70% of human bodies consist of water, and by deriving the BH correction coefficients using a water phantom having a composition similar to that of human body, there can be obtained an advantage that accuracy of the BH correction is improved. Further, the CT value corresponding to the density of CT image is defined as a value obtained by normalizing the density so that the difference of the densities of air and water becomes 1000 (henceforth referred to as CT value normalization), and then subtracting 1000 from the normalized density, and a unit called Hounsfield unit (HU) is used for it. When a water phantom is used, there is obtained an advantage that the BH correction and CT value normalization can be simultaneously carried out by calculating the values of the projection data $p_o$ for a monochromatic X-ray shown in FIG. 20 with assuming that $p_o = 1000L$.

Further, Patent document 3 discloses a method for deriving the BH correction function without using measurement of a phantom. According to the method of Patent document 3, the BH correction function is directly calculated by using the known ray-trace simulation or Monte Carlo simulation. Therefore, it has an advantage that such a phantom measurement operation as used in Patent document 1 or 2 can be omitted.

PRIOR ART REFERENCES

Patent Documents

Patent document 1: Japanese Patent Publication (KOKOKU) No. 61-54412

Patent document 2: Japanese Patent Unexamined Publication (KOKAI) No. 5-130987
Patent document 3: Japanese Patent Unexamined Publication (KOKAI) No. 2006-334319

DISCLOSURE OF THE INVENTION

Object to be Achieved by the Invention

The BH correction method disclosed in Patent document 1 requires measurements of polyethylene phantoms of different sizes for obtaining measured sample data of the BH correction function. In order to increase the number of the measurement samples to improve the accuracy of the BH correction, it is necessary to increase the number of the kinds of the polyethylene phantom, but it causes a problem that the number of the measurement increases to increase the operation cost. Further, since it is generally necessary to produce the polyethylene phantoms for every X-ray CT device as accessories of the device, it has a problem that increase of the number of kinds of the polyethylene phantom invites increase of the production cost. Furthermore, when the aforementioned CT value normalization is taken into consideration, the CT value normalization cannot be performed only with the measurement data for the polyethylene phantom, because of the definition of the CT value normalization. Therefore, the method of Patent document 1 requires separate measurement of a water phantom for performing the CT value normalization, and thus it has a problem that it suffers from increase of operation cost and production cost required for the measurement of the water phantom.

As described above, in the BH correction method disclosed in Patent document 1, three or four kinds of polyethylene phantoms and water phantom are usually used in consideration of the trade-off of accuracy of the BH correction, and operation and production costs. Since the number of measurement samples of the BH correction function used in this method is three or four at most, it has a problem that it is difficult to improve approximation accuracy of the polynomial fitting, and thus it is difficult to obtain higher precision of the BH correction.

In the BH correction method disclosed in Patent document 2, the BH correction can be performed by using only the measurement data of water phantom, and therefore it has such advantages as that the production cost and operation cost can be reduced, and the measurements for the BH correction and the CT value normalization can be simultaneously performed. However, when the BH correction is performed by using only the measurement data of a water phantom, it is necessary to take the X-ray absorption coefficient of the container of the water phantom into consideration. That is, the water phantom consists of a cylindrical container inside of which is filled with water, and X-ray beam BM that transmits through both the container and water are measured as projection data thereof. Therefore, the theoretical value of the projection data for a monochromatic X-ray cannot be simply obtained from the X-ray transmission path length in the phantom, and the ratio $\alpha$ of the X-ray absorption coefficients of the container $\mu_c$ and water $\mu_w$ for a monochromatic X-ray ($\alpha = \mu_c/\mu_w$) is required for the calculation.

However, since the value of $\alpha$ is not known, the BH correction coefficients cannot be obtained by the same method as that of Patent document 1. Therefore, the method of Patent document 2 employs a method of deriving the BH correction coefficients by using a reconstructed CT image of the water phantom so that the CT value of water moiety in the CT image should become a predetermined value. However, this method has a problem that it requires much calculation time due to many CT reconstruction operations performed in the calculation process.

The BH correction method disclosed in Patent document 3 does not require measurement of a phantom for deriving the BH correction coefficients, and therefore it is the most advantageous in view of both the operation cost and production cost. The same method as disclosed in Patent document 1 can be used for deriving the BH correction coefficients, and simulation values can be used instead of actually measured values for a projection image of a polyethylene phantom. Since phantom data for phantoms of various sizes can be calculated by simulation, it is also easy to increase the number of measurement samples of projection data. Further, since a virtual water phantom not including a container can also be used for the simulation, the BH correction coefficients for simultaneously performing the BH correction and the CT value normalization can be easily derived by using the aforementioned virtual water phantom instead of a polyethylene phantom.

However, this BH correction method has a problem that insufficient simulation accuracy results in reduction of correction accuracy. Especially for factors of which reproduction by simulation is difficult, such as variation of characteristics of X-ray detection elements, the aforementioned problem becomes more serious. For example, in actual X-ray detectors, variations of the characteristics of scintillators, which are constituents of the X-ray detection elements, originating in variations of arrangement or production thereof results in individual differences in the energy sensitivity characteristics of the X-ray detection elements. Such individual differences of energy sensitivity characteristics constitute a cause of generating concentric circular artifacts or band-shaped artifacts in reconstructed CT images. In the methods disclosed in Patent documents 1 and 2, such individual differences as mentioned above are measured as actually measured data, and therefore the aforementioned concentric circular artifacts or band-shaped artifacts can be removed by the BH correction. However, in the method of Patent document 3, reproduction of the aforementioned individual differences by simulation is difficult, and therefore such artifacts as mentioned above cannot be removed.

An object of the present invention is to improve quantitative determination ability for CT values and reduce ring-shaped artifacts or band-shaped artifacts by improving accuracy of the BH correction in an X-ray CT device, and thereby provide more accurate diagnostic information for users.

Another object of the present invention is to reduce the number of phantoms and the number of phantom measurement in the phantom measurement for deriving BH correction coefficients, and thereby reduce the production cost of the phantom and the operation cost of the measurement, with maintaining high BH correction accuracy.

A further object of the present invention is to reduce the operation cost of the measurement and the production cost of the phantom by standardizing the measurement for the BH correction and the CT value normalization. A still further object of the present invention is to reduce the calculation cost required for deriving the BH correction coefficients.

Means for Achieving the Object

Hereafter, outlines of typical aspects of the present invention disclosed in this specification will be briefly explained.

<X-Ray CT Device>

The X-ray CT device of the present invention comprises an X-ray generation part, an X-ray detection part oppositely disposed to the X-ray generation part and having a plurality of X-ray detection elements, a correction part for correcting data detected by the X-ray detection part, and an image reconstruction part for reconstructing a CT image by using corrected data, wherein the correction part comprises a beam hardening correction part for correcting the detected data on the basis of a BH correction function representing relation between a target value of X-ray absorption characteristic of a predetermined subject and X-ray absorption characteristic of the predetermined subject under the influence of beam hardening, and the beam hardening correction part comprises an X-ray absorption characteristic calculation part for calculating X-ray absorption characteristic by using an error between a simulation-calculated value of X-ray absorption characteristic obtained beforehand for a virtual subject by simulation and an actually measured value of X-ray absorption characteristic of a subject equivalent to the virtual subject, and a BH correction function calculation part for calculating a BH correction function by using the X-ray absorption characteristic calculated by the X-ray absorption characteristic calculation part, and corrects data measured for a test object on the basis of the BH correction function calculated by the BH correction function calculation part.

In the X-ray CT device of the present invention, data for the correction to be used by the X-ray absorption characteristic calculation part and the BH correction function calculation part can be calculated beforehand by using the same or another X-ray CT device or an independent calculation device, stored as a table, and used.

Since the X-ray CT device of the present invention calculates the X-ray absorption characteristic by using error between a simulation-calculated value and an actually measured value of the X-ray absorption characteristic, it can provide a highly precise BH correction coefficient reflecting variation of characteristics of individual X-ray detection elements with a few actually measured values. Highly precise BH correction is thereby enabled, and improvement of quantitative determination ability for CT value and reduction of ring-shaped artifacts or band-shaped artifacts can be realized.

<Calculation Device for Calculating Data for BH Correction>

The calculation device of the present invention is a calculation device for calculating data for BH correction to be used for the beam hardening correction in an X-ray CT device, and comprises a first calculation part for calculating projection data including influence of the beam hardening effect for a plurality of kinds of virtual phantoms consisting of water phantoms constituted with containers filled with water and providing different X-ray transmission path lengths under a plurality of kinds of imaging conditions by simulation, and calculating simulation calculation values S of X-ray absorption characteristic indicating relation between the X-ray transmission path length and projection data, and a second calculation part for calculating target values T of the X-ray absorption characteristic not including the beam hardening effect for a plurality of kinds of the virtual phantoms, and the second calculation part comprises an image reconstruction means for reconstructing a CT image by using the projection data calculated by simulation for the virtual subject or projection data actually measured for a subject equivalent to the virtual subject, calculates ratios ($\alpha$) of X-ray absorption coefficients of the containers of the virtual phantoms and water from profile of the CT image, and calculates the target values T of the X-ray absorption characteristic by using the ratios.

Alternatively, the calculation device of the present invention comprises, in addition to the first calculation part and the second calculation part of the aforementioned calculation device, a third calculation part for calculating a BH correction function by using the simulation-calculated values S calculated by the first calculation part with assuming that thickness of the containers of the virtual phantoms is 0, and the target values T calculated by the second calculation part, and the second calculation part applies the BH correction function calculated by the third calculation part to the simulation-calculated values S calculated by the first calculation part for the virtual phantoms in which thickness of the containers is variously changed to calculate simulation values corrected by the BH correction as the target values T of the X-ray absorption characteristic.

With the calculation device of the present invention, data for correction used for deriving a BH correction function can be easily created and provided in an X-ray CT device having a function of calculating a BH correction function using a water phantom contained in a container, which is a practically favorable phantom. The data for correction created with the calculation device of the present invention can be commonly used in a plurality of X-ray CT devices.

<Recording Medium for X-Ray CT Devices>

The recording medium for X-ray CT devices of the present invention is a recording medium for X-ray CT devices saving data for BH correction to be used for the beam hardening correction in an X-ray CT device, and the data for BH correction are data for BH correction created by an operation part of an X-ray CT device or the aforementioned calculation device, and consist of simulation-calculated values S of X-ray absorption characteristic including the influence of the beam hardening effect and target values T of X-ray absorption characteristic not including the influence of the beam hardening effect for a plurality of kinds of virtual phantoms providing different X-ray transmission path lengths.

In this recording medium for X-ray CT devices, the data for BH correction may further contain X-ray transmission path lengths of water moieties calculated for a plurality of kinds of the virtual phantoms.

<Maintenance Method>

The method for maintaining X-ray CT devices of the present invention comprises the step of performing imaging of a plurality of kinds of phantoms under a plurality of kinds of imaging conditions to obtain actually measured values of X-ray absorption characteristic for a plurality of kinds of the phantoms, the step of inputting simulation-calculated values of the X-ray absorption characteristic obtained beforehand by simulation for virtual phantoms equivalent to a plurality of kinds of the phantoms to calculates errors between the simulated values and the actually measured values, the step of revising the simulation-calculated values by using the errors, the step of inputting target values of X-ray absorption characteristic calculated beforehand and calculating BH correction coefficients by using the target values and the revised simulation-calculated values of the X-ray absorption characteristic, and the step of saving the calculated BH correction coefficients as a table.

With this maintenance method, highly accurate BH correction coefficients reflecting variation of characteristics of individual X-ray detection element can be set in an X-ray CT device and can provide more accurate diagnostic information for users, even with a small number of phantoms and a small number of measurements.

Other features and effects of the present invention will be explained in detail in the following explanation of the embodiments of the present invention.

MODES FOR CARRYING OUT THE INVENTION

Hereafter, exemplary embodiments of the present invention will be explained in detail with reference to the drawings.

<Configuration of X-Ray CT Device>

Figure 1:
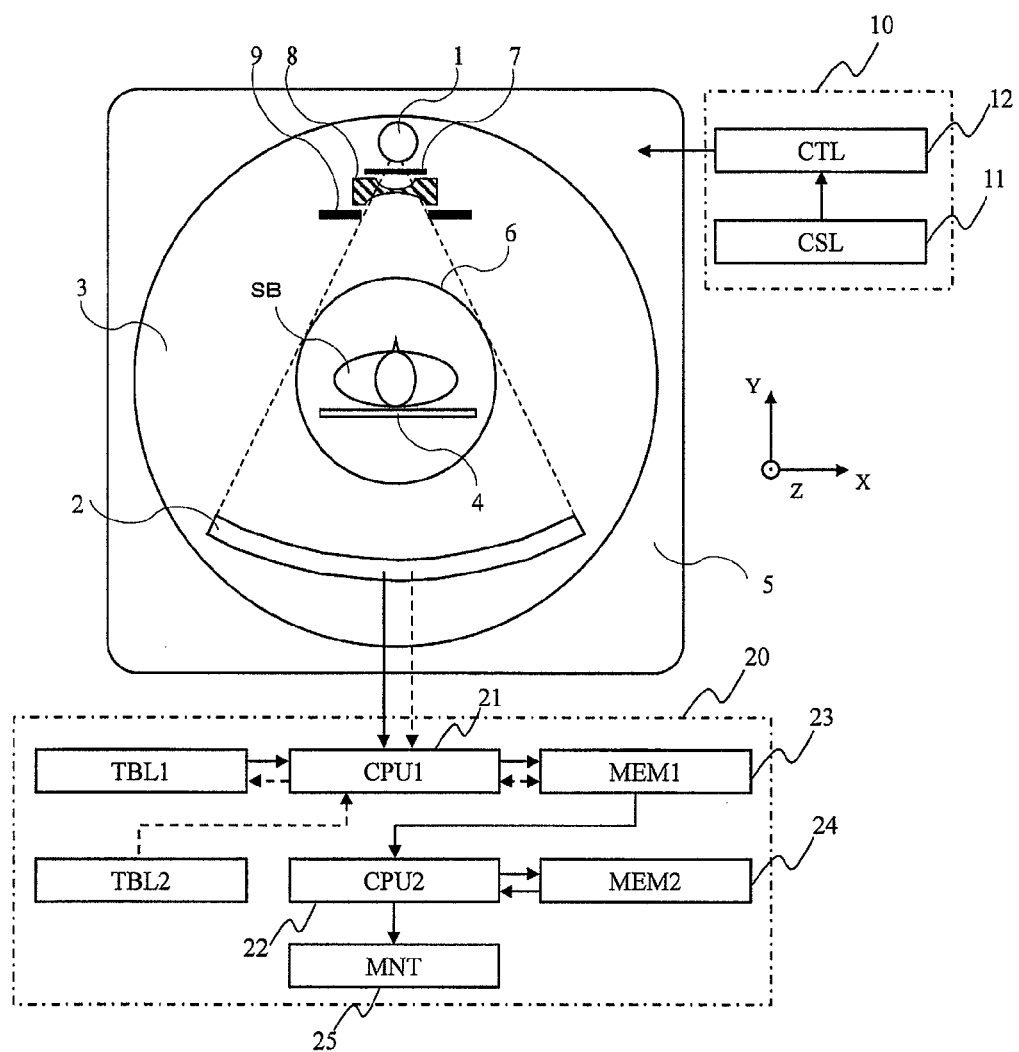
FIG. 1 is a schematic view showing outline of an example of the X-ray CT device of the present invention.

FIG. 1 is a schematic front view of an X-ray CT device according to an embodiment of the present invention. In FIG. 1, the right-and-left direction, the up-and-down direction, and the direction perpendicular to the drawing are defined as X, Y, and Z directions, respectively.

The X-ray CT device according to this embodiment consists of an X-ray tube 1, an X-ray detector 2, a turntable 3, a top of bed 4, a gantry 5, a filters that change X-ray quality (hereinafter referred as radiation quality filter) 7, a bow tie filter 8, a collimator 9, a control system 10, a signal processing system 20, and so forth. The control system 10 comprises an operation console 11 having a display, and an imaging controller 12. The signal processing system 20 performs operations such as correction and image processing for data detected with the X-ray detector 2, and comprises a first operation part 21 for mainly performing operations for correction such as pre-processing, a second operation part 22 for mainly performing image reconstruction and image processing, memories 23 and 24, a monitor 25, and so forth. The X-ray tube 1, the radiation quality filter 7, the bow tie filter 8, the collimator 9, and the X-ray detector 2 are disposed on the turntable 3, and henceforth these are collectively referred to as rotational imaging system.

The rotational imaging system is accommodated, as a whole, inside the gantry 5. An opening 6 is provided at the center of the gantry 5, and a subject SB is placed around the center of the opening 6. In this embodiment, a human body is supposed as the subject SB, and the subject SB is usually laid on the top of bed 4. The turntable 3 is rotated by a driving motor not shown in the drawing, and thus X-ray transmission images of the subject SB are obtained from all the radial directions. The turntable 3 rotates around a rotation axis parallel to the Z direction and passing the center of the opening 6 as the center. The position of the top of bed 4 can be moved along the Z direction by a driving apparatus not shown in the drawing. It is also possible to perform the known helical scan by simultaneously revolving the turntable 3 and moving the top of bed 4.

In the device of FIG. 1, the distance between X-ray generation point of the X-ray tube 1 and X-ray entering surface of the X-ray detector 2 is typically, for example, 1040 [mm]. Further, the diameter of the opening 6 is typically, for example, 650 [mm]. The revolving speed of the turntable 3 is typically, for example, 3 [revolutions/second]. The number of times of imaging in one revolution of the rotational imaging system is typically, for example, 1000 times, and in this case, one time of imaging is performed whenever the turntable 3 revolves 0.36 degree.

The radiation quality filter 7 is a known element constituted by piling up metal plates of a single kind of material or a plurality of kinds of materials, or the like. The radiation quality filter 7 is disposed in the middle of the pathway of the X-ray beam irradiated from the X-ray tube 1 towards the X-ray detector 2, and has a function of changing radiation quality (energy spectrum) of the X-ray passing through the radiation quality filter 7. It is used especially for the purpose of reducing exposure of the subject SB by shielding a low energy X-ray, or reducing the influence of the BH effect. Typical examples of metal plate used for the radiation quality filter 7 include a copper plate having a thickness of about 0.05 to 0.2 mm, an aluminum plate having a thickness of about several millimeters, one obtained by piling these up, and so forth. In the device of this embodiment, a plurality of kinds of the radiation quality filters 7 are prepared, and a user can choose a suitable one among them depending on the purpose of imaging. A radiation quality filter 7 specified as described above is disposed in the middle of the pathway of the X-ray beam in advance of imaging by a moving mechanism not shown in the drawing.

The bow tie filter 8 is a known component formed with such a material as aluminum. The bow tie filter 8 is disposed in the middle of the pathway of the X-ray beam irradiated from the X-ray tube 1 towards the X-ray detector 2. The bow tie filter 8 has such a shape that the thickness thereof changes so that the transmission path length of the X-ray beam in the bow tie filter 8 should become shortest at the center of the opening 6 and become longer as the position of the X-ray beam approaches the circumference thereof. With such a bow tie filter, intensity of the X-ray having passed through the subject SB and entering into the X-ray detector 2 is made uniform for the XY plane direction (direction parallel to the XY plane, the same shall apply in the following descriptions). As a result, there is obtained an effect that graininess of noises at the center part and circumferential part of the subject can be made uniform in the finally obtained CT image of the subject SB, and the visibility of the CT image can be thereby improved. Moreover, it also provides an effect that exposure of the subject SB at circumferential positions can be reduced. In the device of this embodiment, the bow tie filters 8 having a plurality of kinds of shapes are prepared for various sizes and imaging positions of the subject SB, and a user can choose a suitable kind of the bow tie filter 8. A bow tie filter 8 specified as described above is disposed in the middle of the pathway of the X-ray beam in advance of imaging by a moving mechanism not shown in the drawing.

The collimator 9 is a known X-ray shielding panel formed with such a material as lead, and limits the irradiation area of the X-ray irradiated from the X-ray tube 1 for the XY plane direction and the Z direction. The irradiation area of the aforementioned X-ray for the XY plane direction is limited so that it corresponds to the input area of the X-ray detector 2 for the XY plane direction. Further, a user can variously change the irradiation area for the Z direction (henceforth referred to as slice width) depending on the purpose of the imaging. For such a purpose, the collimator 9 is moved with a moving mechanism not shown in the drawing so that the slice width is limited to a specified size.

Figure 2:
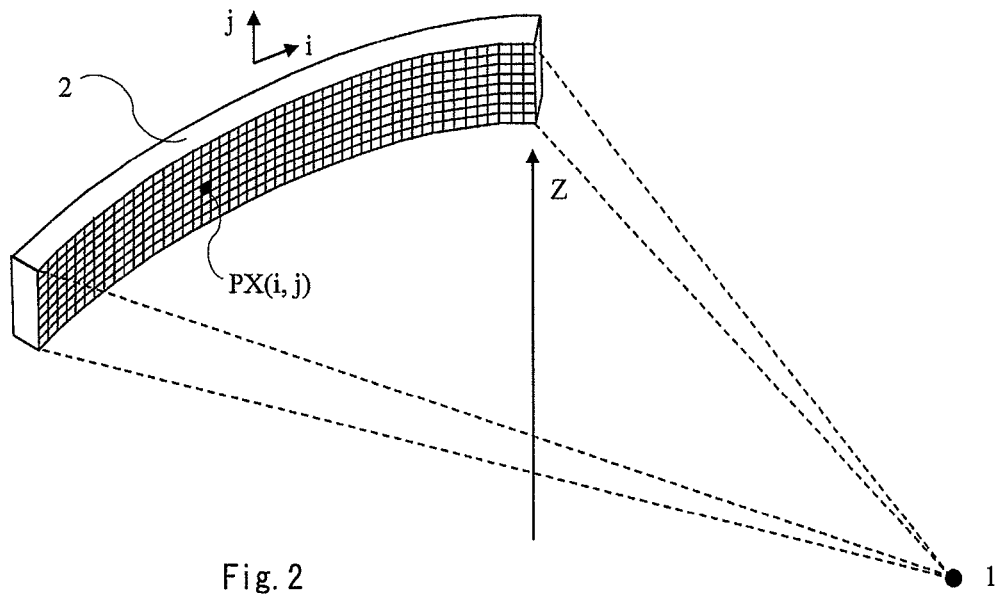
FIG. 2 is a perspective view showing details of an X-ray detector.

The X-ray detector 2 is a known component consisting of a scattered ray removing collimator, a scintillator array, a photodiode array, and so forth, which are not shown in the drawing. As shown in FIG. 2, the X-ray detector 2 has a two-dimensional input surface consisting of many X-ray detection elements arranged in the form of a matrix, and it is disposed so that this input surface faces the X-ray tube 1. The number of the arranged X-ray detection elements is typically, for example, 1000 (XY plane direction)×64 (Z direction). The X-ray detection elements are arranged on a circular arc remote from the X-ray tube 1 by substantially the same distance for the XY plane direction. The size of each X-ray detection element for the XY plane direction and the Z direction is typically, for example, 1 [mm].

In the following explanation, each X-ray detection element is represented as PX(i, j). i and j represent positions of the X-ray detection element for the direction perpendicular to the Z-axis, and the direction parallel to the Z-axis, respectively. In the following explanation, the direction along which position represented with i is also referred to as channel direction, and the direction along which position is represented with j is also referred to as slice direction.

The operation console 11 is for inputting imaging conditions such as tube voltage, tube current, revolving speed of the turntable 3, slice width, kinds of the radiation quality filter 7 and the bow tie filter 8, and imaging area of the subject SB, as well as selection, start and end of operation mode, and has a keyboard, a display for displaying GUI, etc.

The imaging controller 12 moves various filters etc. according to the imaging conditions inputted from the operation console 11, and controls operations of the turntable 3, the X-ray tube 1, and the X-ray detector 2 under the selected operation mode.

The first operation part 21 of the signal processing system 20 comprises a reference correction part, an air correction part, a BH correction part, and so forth, performs pre-processings such as reference correction, air correction, and BH correction for raw data detected by the X-ray detector 2, and saves the corrected data in the memory 23. The data required for the pre-processings (values of reference data, air data, and BH correction coefficients etc.) are stored in the table TBL1 beforehand, and the first operation part 21 read out these data from the table TBL1, and performs the corrections. Further, the first operation part 21 may also have a function of calculating the BH correction coefficients to be described later. The data required for this calculation are stored in the table TBL2.

The second operation part 22 reconstructs a CT image by using the corrected data saved in the memory 23, and saves image data in the memory 24. The second operation part 22 reads out the CT image data from the memory 24, creates a CT image for display by a known image processing technique, such as the volume rendering method, the MIP (Maximum Intensity Projection) method and the MPR (Multi Planar Reconstruction) method, and displays it on a screen of the monitor 25.

For the first operation part 21 and the second operation part 22, an exclusive calculation unit or a known general-purpose calculation unit can be used. Further, for the memory 23, memory 24, table TBL1, and table TBL2, known recording means, such as RAM (Random Access Memory), hard disk, SSD (Solid State Drive), a combination of these, and so forth are used.

<Operation of X-Ray CT Device>

Hereafter, operation of the X-ray CT device of this embodiment will be explained. This X-ray CT device can operate in two kinds of measurement modes, i.e., main measurement mode and maintenance measurement mode. Selection of the main measurement mode or the maintenance measurement mode is specified through the operation console 11. Imaging in the maintenance measurement mode is imaging for obtaining the correction parameters used by the first operation part 21, and is usually performed by only maintenance operators. Imaging in the main measurement mode is imaging for obtaining a CT image of an object of examination, and general users use only the main measurement mode. In FIG. 1, the data flow in the measurement according to the main measurement mode is represented with arrows of solid line, and the same according to the maintenance measurement mode is represented with arrows of broken line.

<Operation in Main Measurement Mode>

Figure 3:
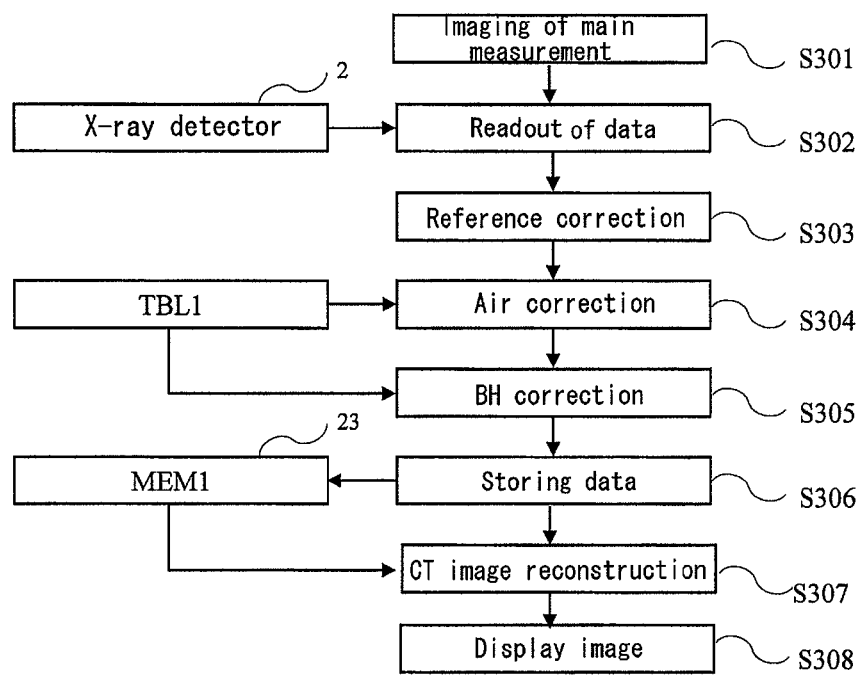
FIG. 3 is a flowchart showing the imaging procedure of the main measurement mode.

First, operation of the X-ray CT device in the main measurement mode will be explained with reference to FIG. 3. A user sets imaging conditions, and directs start of imaging through the operation console 11. When start of imaging is directed, the imaging controller 12 starts rotation of the turntable 3, and when a specified constant speed rotation state of the turntable 3 is attained, it directs start of X-ray irradiation from the X-ray tube 1 and start of detection with the X-ray detector 2 to start imaging (Step S301).

The imaging is performed a plurality of times, typically about 1000 times, in every one revolution of the turntable 3, and the signal processing system 20 reads imaging data for every imaging (Step S302). The imaging data consist of X-ray intensities I detected by the X-ray detection elements PX(i, j, m) (m represents an imaging number).

The first operation part 21 performs the reference correction, air correction, and BH correction for the read imaging data as pre-processings (Steps S303 to S305). The reference correction is a processing for normalizing output change of the X-ray irradiated from the X-ray tube 1, and is performed by dividing raw data $I_{raw}$ with reference data $I_{ref}$ in accordance with the following equation (2).

[Equation 2]

$$I(i,j,m) = I_{raw}(i,j,m)/I_{ref}(m) \quad (2)$$

As the value of the reference data $I_{ref}(m)$, there is usually used an average of the imaging data of X-rays not passing through the subject SB and detected by the X-ray detection elements near both ends of the X-ray detector 2 for the i direction.

The air correction is an operation for normalizing the imaging data of the subject with data of imaging performed without placing the subject (air data), and it is performed in accordance with the following equation (3).

[Equation 3]

$$p(i,j,m) = -\ln(I(i,j,m)/I_o(i,j)) \quad (3)$$

The air data $I_o(i, j)$ are obtained by performing the reference correction for the imaging data $I_o(i, j, m)$ obtained without placing the subject SB and the top of bed 4, and averaging the corrected data for the m direction. Air data measured beforehand for all of a plurality of kinds of imaging conditions realizable with the X-ray CT device are recorded in the table TBL1. At the time of the air correction, the first operation part 21 reads out air data of the corresponding imaging condition from TBL1 and performs calculation of the equation (3). Data corrected by the air correction are henceforth referred to as projection data.

The BH correction is a processing for eliminating the influence of the BH effect caused by use of a polychromatic X-ray, in which projection data are corrected in accordance with following equation (4) on the basis of the relation between X-ray absorption characteristic obtained by supposedly using a monochromatic X-ray and X-ray absorption characteristic obtained by using a polychromatic X-ray for a predetermined subject.

[Equation 4]

$$p_o(i,j,m) = a_1(i,j)p(i,j,m) + a_2(i,j)p(i,j,m)^2 + \ldots + a_K(i,j)p(i,j,m)^K \quad (4)$$

In the equation, $a_1(i, j), a_2(i, j), \ldots, a_K(i, j)$ are coefficients (BH correction coefficients) of the items of the item-expanded BH correction function, and those calculated for a plurality of kinds (H kinds) of imaging conditions are recorded in the table TBL1.

Typical examples of the parameters specifying the imaging condition are three kinds of conditions, the tube voltage of the X-ray tube 1, the kind of the radiation quality filter 7, and the kind of the bow tie filters 8, and the BH correction coefficients are calculated for all the combinations of these three kinds of parameters, and stored. For example, if there is supposed a case where two kinds of the tube voltages (100 kV, 120 kV), three kinds of the radiation quality filters 7, and two kinds of the bow tie filters 8 are prepared, the total numbers of the combinations of the imaging conditions H is 12 (=2×3×2). The aforementioned 3 kinds of parameters change the radiation quality of X-ray, and therefore have influence on the BH effect.

Figure 4:
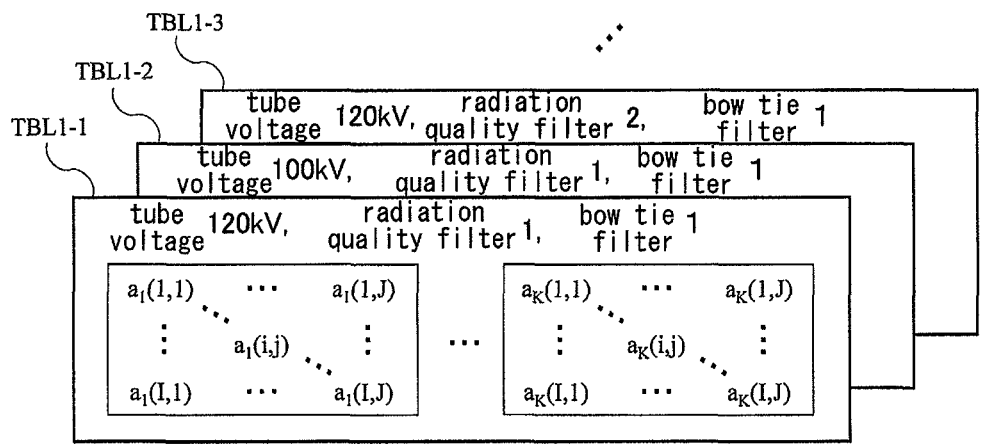
FIG. 4 is a drawing for explaining content of data of BH correction coefficients to be saved in a table TBL1.

An example of the content of data of the BH correction coefficients saved in the table TBL1 is shown in FIG. 4. As shown in the drawing, the BH correction coefficients are made up into a small table for every imaging condition specified by a combination of three kinds of the parameters, the tube voltage of the X-ray tube 1, the kind of the radiation quality filter 7, and the kind of bow tie filter 8, and stored for all the imaging conditions of H kinds as TBL1-1, TBL1-2, TBL1-3, . . . , and TBL1-H. In each small table, the BH correction coefficients $a_1(i, j), a_2(i, j), \ldots$, and $a_K(i, j)$ calculated for every X-ray detection element PX(i, j) are recorded. The correction part (BH correction part) 21 performs the calculation of the equation (4) by reading out the BH correction coefficients of the corresponding imaging condition from such table TBL1 at the time of the BH correction.

The first operation part 21 saves the imaging data $p_o(i, j, m)$ corrected by the BH correction in the memory 23 (Step S306). Whenever the X-ray detector 2 obtains m-th new imaging data, a series of the processings of Steps S302 to S305 are repeatedly carried out.

If imaging in a set number of times is completed, and re-imaging is not directed, the imaging controller 12 terminates the operations of the X-ray tube 1, the X-ray detector 2, and the turntable 3. Further, the second operation part 22 reads out projection data obtained by all the number of times of imaging from the memory 23, reconstructs a CT image by a known reconstruction method (Step S307), further creates a display image of the CT image by using a known image processing technique, and displays it on the screen of the monitor 25 (Step S308).

<Operation of Maintenance Measurement Mode>

Hereafter, operation of the X-ray CT device of the present invention in the maintenance measurement mode will be explained. The measurement in the maintenance measurement mode is performed in order to obtain data required for calculating correction parameters used in the main measurement mode, such as the BH correction coefficients. A case where the phantom is a water phantom will be explained below.

Figure 5:
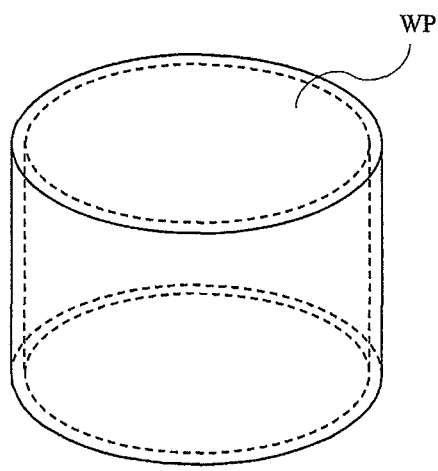
FIG. 5 shows a structure of a water phantom WP used in the maintenance measurement mode.

The shape of the water phantom WP is typically such a cylindrical shape as shown in FIG. 5, and in the maintenance measurement mode, it is disposed so that the center axis of the cylindrical shape substantially corresponds to the rotating axis of the turntable 3. Further, N of water phantoms having different diameters are prepared, and the water phantoms WP will be referred to with a number n (n=1 to N) in the following explanation. N is typically, for example, 4, and the diameters of the water phantoms WP are typically, for example, 100 mm (n=1), 200 mm (n=2), 300 mm (n=3), and 400 mm (n=4).

The measurement in the maintenance measurement mode is performed for all of these water phantoms in a number of N under H kinds of imaging conditions. For example, as mentioned above, the measurement for obtaining the BH correction coefficients is performed with two kinds of the tube voltages (100 kV, 120 kV), three kinds of the radiation quality filters 7, and two kinds of the bow tie filters 8, i.e., under total 12 kinds of imaging conditions (H=2×3×2). Therefore, each of N kinds of the water phantoms WP is imaged H times under all the kinds of the imaging condition, and the total measurement number is N×H times. Although the slice width may be fixed to the maximum slice width (value corresponding to the maximum size of the input surface of the X-ray detector 2 for the Z direction), the amount of scattered X-rays generated within the water phantom WP may change with change of the slice width to influence on the BH effect, and therefore the slice width may be included in the aforementioned imaging conditions as the fourth parameter.

Figure 6:
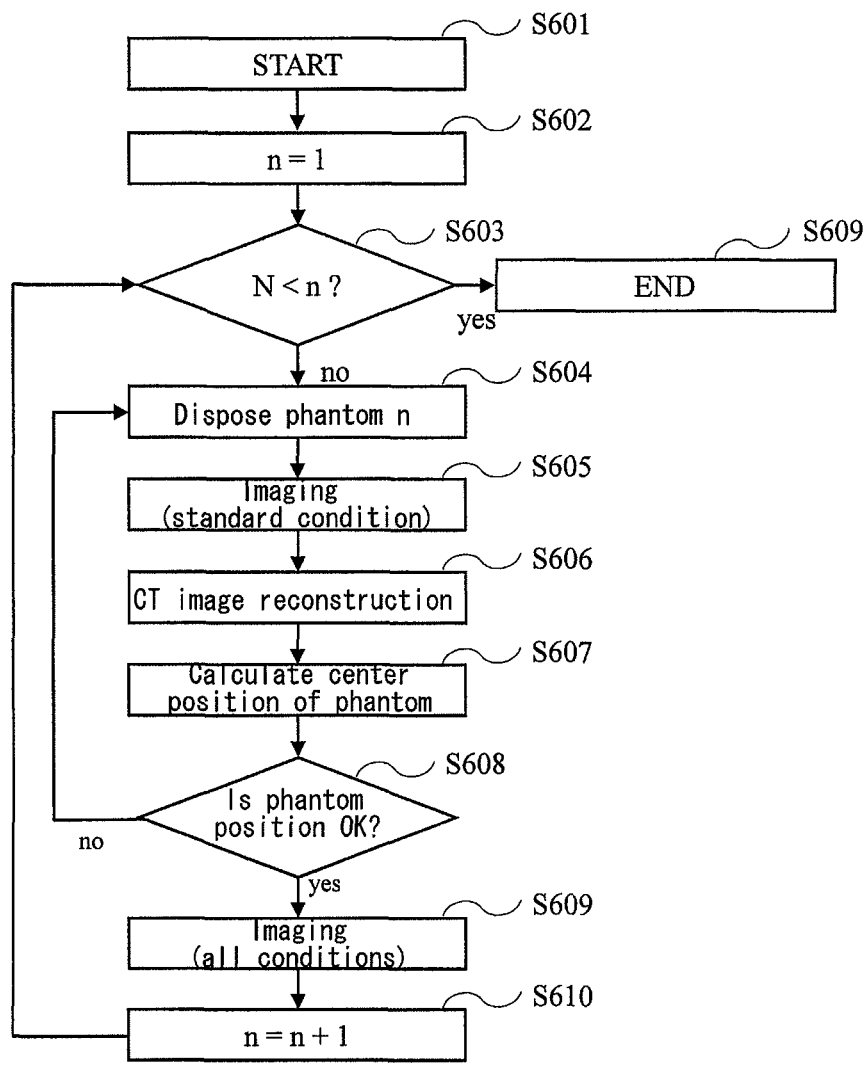
FIG. 6 is a flowchart showing the imaging procedure of the maintenance measurement mode.

The procedure of the imaging is shown in FIG. 6. First, when a maintenance worker starts imaging of the water phantoms (Step S601), 1 is set as the first phantom number n (Step S602). Then, it is judged whether the phantom number n is larger than the total number N of the kinds of the water phantoms (Step S603), and when it is judged to be Yes, all the imaging is ended (Step S609). When it is judged to be No in Step S603, the maintenance worker disposes a water phantom of the phantom number n in the central opening of the turntable 3 (Step S604). At this time, the water phantom is disposed so that the center axis of the cylinder of the water phantom substantially corresponds to the rotating axis of the turntable 3.

After disposition of the water phantom is completed, the maintenance worker performs imaging of the disposed water phantom under a predetermined standard imaging condition specified beforehand (Step S605).

As in the imaging in the main measurement mode, the imaging controller 1 first starts rotation of the turntable 3, and when a specified constant speed rotation state of the turntable 3 is attained, it directs start of X-ray irradiation from the X-ray tube 1 and start of detection with the X-ray detector 2 to start imaging. Imaging data outputted from the X-ray detector 2 are subjected to pre-processings (reference correction and air correction) performed by the first operation part 21, and the projection data corrected by the air correction are successively saved in the memory 23.

Then, the data obtained by the imaging are subjected to pre-processings and reconstruction operation processings according to the same procedure as the calculation procedure shown for the main measurement mode to calculate a CT image of the water phantom (Step S606). On the basis of this CT image, the center axis position of the water phantom is calculated by the second operation part 22 (Step S607). The center axis position can be easily calculated as the position of the center of gravity of the water phantom in the CT image. Then, on the basis of the calculation result of the center axis position, it is judged whether the water phantom has been disposed at a proper position, and the result of the judgment is displayed on the monitor 25 (Step S608). As for example of the judgment criterion, there is used a method of judging Yes when the distance between the position of the center of gravity of the water phantom and the rotating axis of the turntable 3 is not larger than a predetermined threshold value (for example, 1 mm), or No when the aforementioned condition is not satisfied. When it is judged to be No in Step S608, the process returns to Step S604, and the maintenance worker adjusts the position of the water phantom. The procedure of Steps S604 to S608 is repeated until it is judged to be Yes in Step S608.

When it is judged to be Yes in Step S608, imaging of the water phantom is then carried out under all of H kinds of the imaging conditions (Step S609). The obtained imaging data are converted into projection data by the pre-processings (reference correction and air correction) as described above, and saved in the memory 23. After the imaging is completed for all the imaging conditions, 1 is then added to the phantom number n (Step S610), and the process returns to Step S603. The aforementioned procedure of Steps S603 to S610 is repeated until it is judged to be Yes in Step S603. All the projection data obtained by each imaging are saved in the memory 23, and imaging in the maintenance measurement mode is ended.

By using the projection data obtained by imaging in the maintenance measurement mode, calculation of the BH correction coefficients explained below is performed.

<Calculation of BH Correction Coefficients>

If X-ray absorption characteristic T of a predetermined phantom for a monochromatic X-ray (namely, not including the BH effect, target value) and X-ray absorption characteristic S of the same phantom for a polychromatic X-ray (namely, including influence of the BH effect) are obtained, the BH correction coefficients can be calculated from a function representing the relation of them (BH correction function). The X-ray absorption characteristic S for a polychromatic X-ray can be calculated by simulation, and Patent document 3 mentioned above discloses a procedure thereof.

Figure 7:
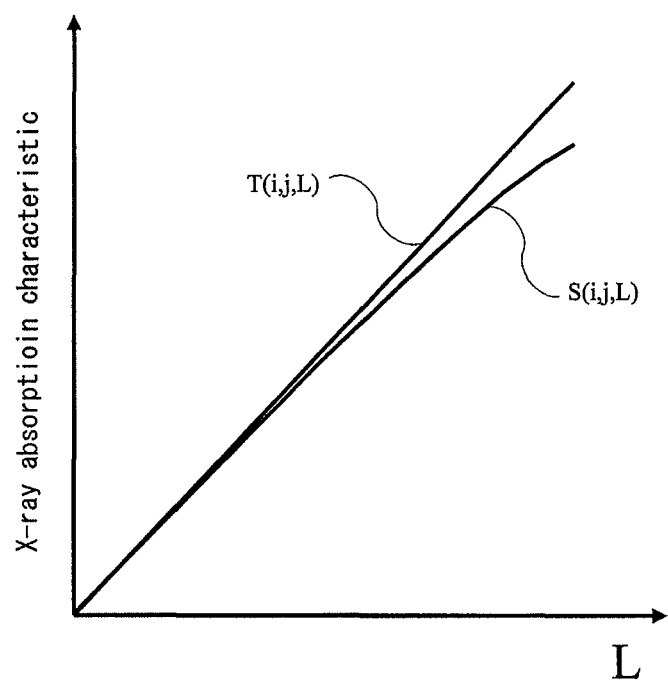
FIG. 7 is a graph showing relation between the simulation value S of X-ray absorption characteristic and the target value T of X-ray absorption characteristic, wherein the X-ray transmission path length L is a variable.

A graph showing the relation of the simulation value S(i, j, L) of the X-ray absorption characteristic and the target value T(i, j, L) of the X-ray absorption characteristic is shown FIG. 7, in which the X-ray transmission path length L is a variable. If it is assumed that the simulation value S(i, j, L) is accurate and equal to the actually measured value, the BH correction can be represented by the equation (5) by using the BH correction function A shown in the equation (1).

[Equation 5]

$$T(i,j,L)=A(S(i,j,L)) \qquad (5)$$

Here, the BH correction coefficients are calculated by the least square method, and since both S(i, j, L) and T(i, j, L) have a sample point for many kinds of path lengths L (=Lu (u=1 to U)), there is an advantage that reduction of the approximation accuracy due to insufficiency of the sample points can be prevented. However, in fact, the simulation value of S(i, j, L) does not necessarily the same as the actually measured value, but there is an error. The causes of the error include insufficiency of the accuracy of the simulation itself, difficulty in reflecting variation of characteristics of the X-ray detection elements resulting from individual differences thereof, shift of positions thereof etc. in simulation conditions, and so forth. Since such an error reduces the accuracy of the BH correction and causes uneven density of the CT image or ring-shaped artifacts, S(i, j, L) must be revised on the basis of a measurement value of the error.

Therefore, in this embodiment, by correcting the X-ray absorption characteristic (simulation value) S obtained beforehand by simulation calculation with actual measurement data (actually measured value) obtained by actually imaging the phantom, highly precise X-ray absorption characteristic S for a polychromatic X-ray is calculated, and the BH correction coefficients are calculated on the basis of it.

<<Table TBL2 Used for Calculation>>

First, data for correction used for the calculation of the BH correction coefficients will be explained. As the target values T and the simulation values S of the X-ray absorption characteristic required for the calculation of the BH correction coefficients, those calculated beforehand for all of a plurality of kinds (H kinds) of the imaging conditions realizable in the X-ray CT device of this invention are stored in the table TBL2. Further, as the path lengths L used for the calculation of the BH correction coefficients, those calculated for a plurality of kinds of phantoms and each element are also stored in the table TBL2.

Figure 8:
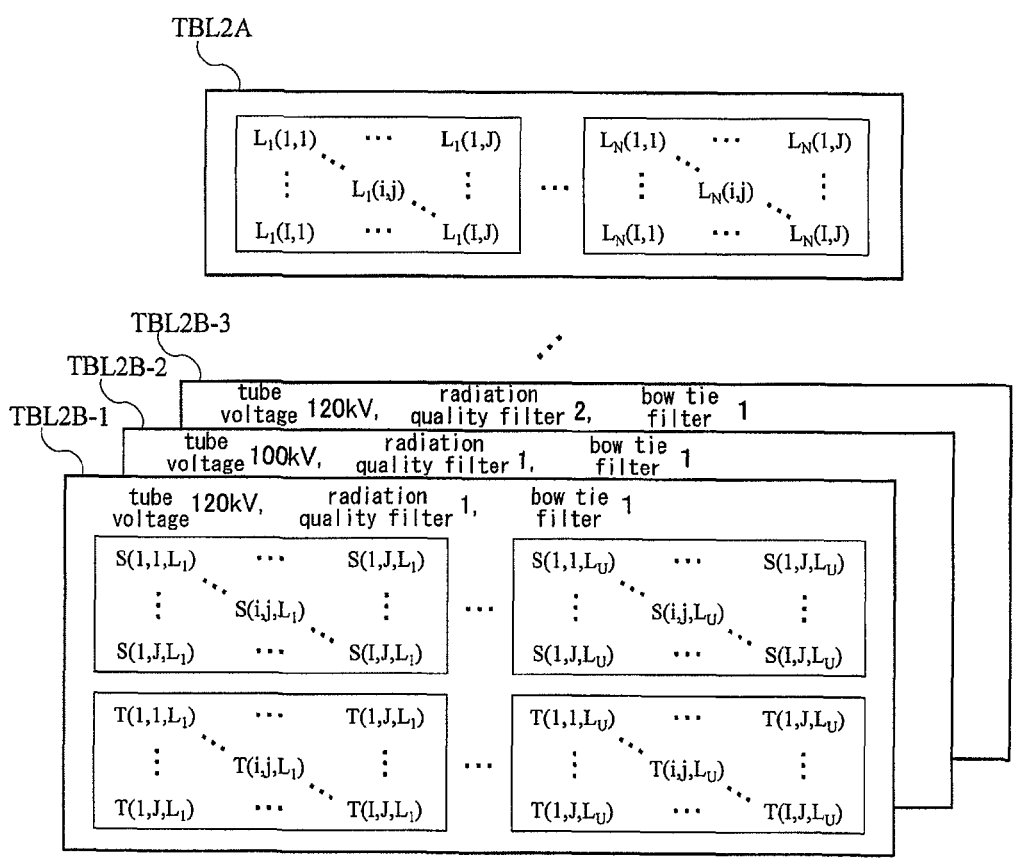
FIG. 8 is a drawing for explaining data content of data for correction saved in a table TBL2 (X-ray transmission path length of water phantom, simulation value of X-ray absorption characteristic, and target value of X-ray absorption characteristic).

The path lengths L of the phantoms, the target values T and the simulation values S of the X-ray absorption characteristic saved in the table TBL2 are shown in FIG. 8. In FIG. 8, TBL2A is a table for storing the path lengths L of the phantoms, TBL2B comprises tables for storing the target values T and the simulation values S of the X-ray absorption characteristic in the same number as that of the imaging conditions.

Figure 9:
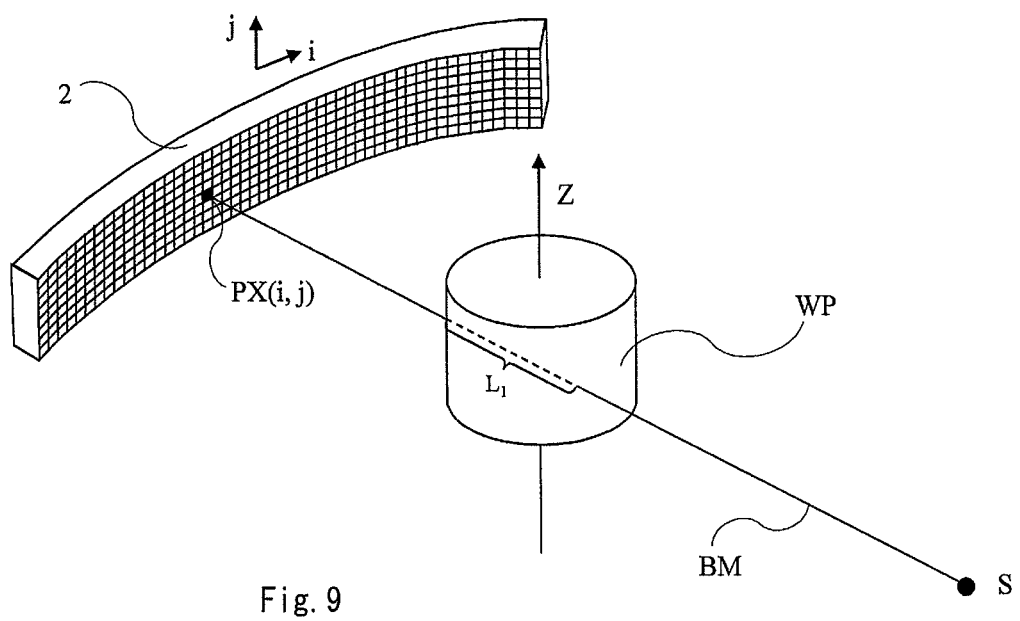
FIG. 9 is a drawing for explaining a method for arranging phantoms for measuring a BH correction function.

The X-ray transmission path length $L_n(i, j)$ of a water phantom is the transmission path length of an X-ray beam in the water phantom WP as shown in FIG. 9, and when the phantom is disposed so that the center axis of the cylinder of the phantom corresponds to the center axis of the turntable 3, it can be geometrically calculated as a length of a straight line connecting the X-ray generation point S and the X-ray detection element PX(i, j) within the water phantom WP. The X-ray transmission path lengths calculated beforehand for to the phantoms of all the numbers of n (n=1 to N) are saved in the table TBL2A.

The simulation value S(i, j, L) of the X-ray absorption characteristic represents a simulation-calculated value of the projection data detected with the X-ray detection element PX(i, j) at an X-ray transmission path length of L. The simulation calculation is carried out for various values of L, $L_1$ to $L_U$, and the calculation results are stored in the form of tables TBL2B-1, TBL2B-2, ..., TBL2 B-H for every imaging condition. The calculation is carried out for values of $L_u$ (u=1 to U) defined with 5 mm units, for example, $L_1$=5 mm, $L_2$=10 mm, ..., $L_{100}$=500 mm, and so forth.

The target value T(i, j, L) of the X-ray absorption characteristic is a target value of the X-ray absorption characteristic converted by the BH correction. T(i, j, L) is calculated for every imaging condition, like S(i, j, L), and the calculation results are also saved in the tables TBL2B-1, TBL2B-2, ..., TBL2 B-H, respectively.

The methods for obtaining the aforementioned target value T and simulation value S of the X-ray absorption characteristic will be described later, and the procedure for calculating the BH correction coefficients using the projection data obtained by the imaging in the maintenance measurement mode and the calculated values saved in the table TBL2 will be explained first.

<<Calculation Procedure>>

Figure 10:
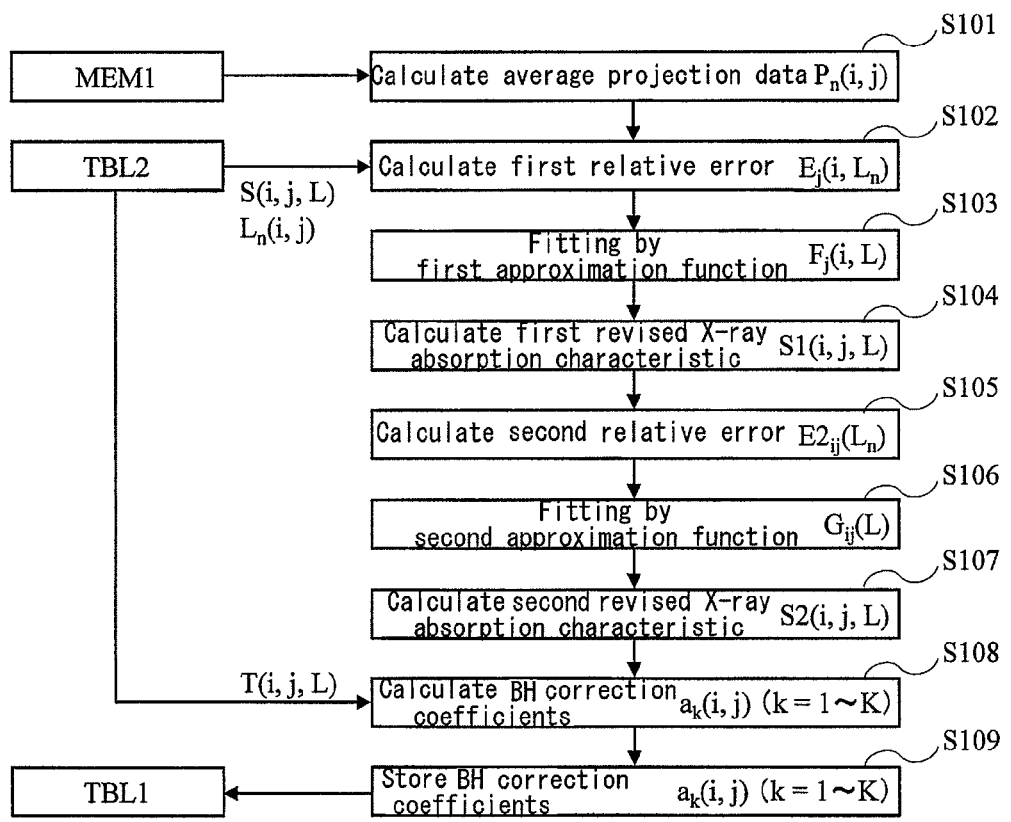
FIG. 10 is a flowchart showing calculation procedure of BH correction coefficients.

The procedure for calculating the BH correction coefficients on the basis of the projection data is shown in FIG. 10. According to this embodiment, this calculation is performed by the first operation part 21.

[Step S101]

When the imaging of the water phantoms is completed, the projection data $p_n(i, j, m)$ are recorded in the memory 23. n (=1 to N) represents a phantom number. The projection data are recorded for each of H kinds of the imaging conditions, and the following calculation is carried out for each imaging condition. First, the projection data $p_n(i, j, m)$ are read out from the memory 23, and average projection data $P_n(i, j)$ are calculated in accordance with the following equation (6).

[Equation 6]

$$P_n(i,j)=1/M\Sigma_{m=1}^{M}p_n(i,j,m) \quad (6)$$

M is the total number of times of imaging. Since the water phantom is usually imaged in the period for one revolution of the rotational imaging system, if the number of times of the imaging in a period of one revolution is 1000 times, the value of M is 1000. However, in order to reduce the signal noises of the average projection data $P_n(i, j)$, the imaging may be performed for a period of a plurality of times of revolution to increase the value of M.

[Step S102]

Then, the X-ray transmission path length $L_n(i, j)$ of the water phantom and the X-ray absorption characteristic simulation value S(i, j, L) are read out from the table TBL2, and a first relative error corresponding to the relative error between the actually measured value and the simulation value of the X-ray absorption characteristic is calculated in accordance with the following equation (7).

[Equation 7]

$$E_j(i,L_n)=P_n(i,j)/S(i,j,L_n(i,j))-1 \quad (7)$$

This calculation of the first relative error mainly calculates an error resulting from scattered X-rays, and is performed for every slice position of the X-ray detector 2. In order to indicate that the calculation is performed for every slice position of the X-ray detector 2, j is used as a subscript in the first relative error $E_j(i, L_n)$.

Figure 11:
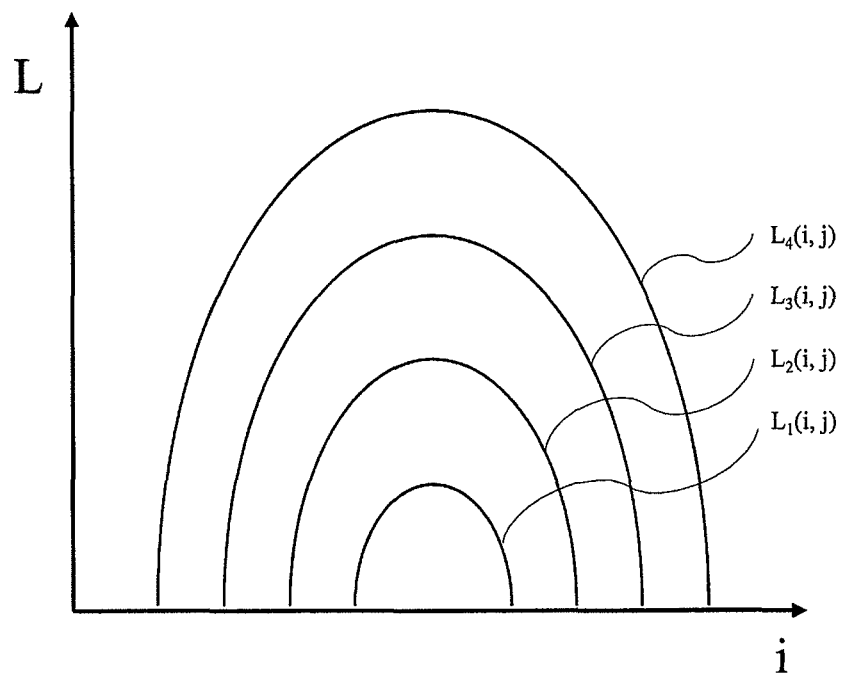
FIG. 11 is a drawing for explaining measurement position for measurement of projection data P on the (i, L) plane.

The aforementioned simulation value S(i, j, L) of the X-ray absorption characteristic is calculated for the total area on the (i, L) plane (correctly, for values of L satisfying the condition $L_1 \leq L \leq L_U$), but the actually measured projection data $P_n(i, j)$ are measured only on the curve (i, $L_n(i, j)$). For example, if the total number N of the kinds of the water phantom to be used is 4, actually measured projection data are obtained only at the positions on the curves $L_1(i, j)$ to $L_4(i, j)$ as shown in FIG. 11. Therefore, the first relative error shown in the equation (7) is also measured only at the positions on the aforementioned curves.

[Step S103]

Then, by using the first approximation function shown as the equation (8), fitting of the first relative error $E_j(i, Ln)$ is performed.

[Equation 8]

$$F_j(i,L)=b_1i^2+b_2L+b_3L^2+b_4i^2L \quad (8)$$

In the equation, $b_1$ to $b_4$ are coefficients of the approximation polynomial, and the values of $b_1$ to $b_4$ can be calculated by carrying out least mean square approximation of the first relative error $E_j(i, Ln)$ with the first approximation function $F_j(i, L)$. The first approximation function is not limited to that of the equation (8), and may be replaced with any of various polynomials using i and L as variables. Further, a part or all of the aforementioned polynomial may be replaced with any of various functions (for example, exponential function, involution function, etc.) using i or L as a variable.

[Step S104]

Then, a first revised X-ray absorption characteristic is calculated by using the first approximation function $F_j(i, L)$ calculated in Step S103 in accordance with the equation (9).

[Equation 9]

$$S1(i,j,L)=S(i,j,L)*(1+F_j(i,L)) \quad (9)$$

As seen from the equation (9), the first revised X-ray absorption characteristic $S_1(i, j, L)$ is obtained by making S(i, j, L) closer to the actually measured value by revising the overall distribution of the errors of S(i, j, L) on the plane (i, L).

[Step S105]

Then, a second relative error is calculated in accordance with the equation (10) by using the first revised X-ray absorption characteristic S1(i, j, L) calculated in Step S104.

[Equation 10]

$$E2_{ij}(L_n) = P_n(i,j)/S1(i,j,L_n(i,j)) - 1 \qquad (10)$$

Since the aforementioned second relative error $E2_{ij}(L_n)$ is calculated for each X-ray detection element of the X-ray detector 2, it contains ij as subscripts. The equation (10) corresponds to the equation of the first relative error of the equation (7) in which S(i, j, L) is replaced with S1(i, j, L). Since non-random error components originating in the theoretic factors of the simulation are excluded from the first revised X-ray absorption characteristic S1(i, j, L), the information included in the aforementioned second relative error $E2_{ij}(L_n)$ corresponds to the random error components generated by characteristic variation of the X-ray detection elements, and so forth.

[Step S106]

Then, fitting of the second relative error $E2_{ij}(L_n)$ is performed by using the second approximation function shown as the equation (11).

[Equation 11]

$$G_{ij}(L) = c_1 + c_2 L + c_3 L^2 \qquad (11)$$

In the equation, $c_1$ to $c_3$ are coefficients of the approximation polynomial, and the values of $c_1$ to $c_3$ can be calculated by carrying out least mean square approximation of the second relative error $E2_{ij}(Ln)$ with the second approximation function $G_{ij}(L)$. The second approximation function is not limited to that of the equation (11), and may be replaced with any of various polynomials using L as a variable. Further, a part or all of the aforementioned polynomial may be replaced with any of various functions (for example, exponential function, involution function, etc.) using L as a variable.

Figure 12:
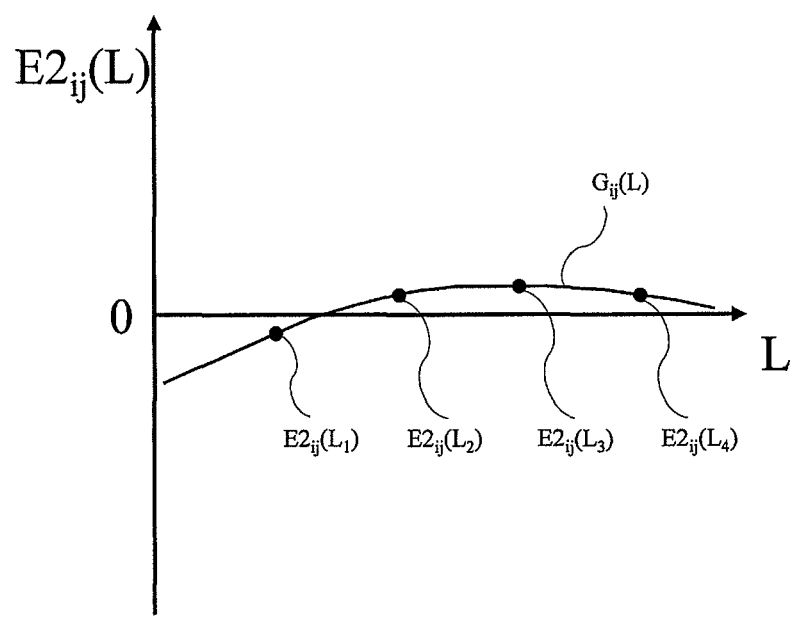
FIG. 12 is a drawing for explaining fitting of the second relative error E2ij(Ln) using the second approximation function Gij(L).

The fitting of the second relative error $E2_{ij}(L_n)$ with the second approximation function $G_{ij}(L)$ is shown in FIG. 12. As explained for the first relative error with reference to FIG. 11, the second relative error $E2_{ij}(L_n)$ is also measured only on the curve (i, $L_n$(i, j)) on the (i, L) plane. Therefore, as shown in FIG. 12, the second relative error $E2_{ij}(L_n)$ is discretely sampled at values of $L=L_1, L_2, \ldots, L_N$. FIG. 12 shows the case where the total number N of the kinds of water phantoms is 4. Since the second relative error $E2_{ij}(L_n)$ is the relative error of the actually measured projection data $P_n$(i, j) and the first revised X-ray absorption characteristic S1(i, j, L), if S1(i, j, L) is correctly calculated to a certain extent, it is considered that change of $E2_{ij}(L_n)$ for the L direction is relatively mild. Therefore, even with such a second approximation function $G_{ij}(L)$ of a low order polynomial as shown in the equation (11), comparatively high fitting accuracy can be secured.

Although an example where the second relative error is sampled at four positions of $L_1$ to $L_4$ is shown in FIG. 12, the number of the samples decreases from 4 to 3, 2, 1, or 0 as the position approaches the both ends for the channel direction (i direction), as shown in FIG. 11. When the sample number is 2 or less, the fitting can no longer be performed with the secondary polynomial shown as the equation (11), and therefore it is necessary to reduce the order of the polynomial. Specifically, when the sample number is 2, the primary polynomial part is used instead of the equation (11), when the sample number is 1, the constant is used instead of the equation (11), and when the sample number is 0, it is assumed that $G_{ij}(L)=0$.

[Step S107]

By using the second approximation function $G_{ij}(L)$ calculated in Step S106, the second revised X-ray absorption characteristic is calculated in accordance with the equation (12).

[Equation 12]

$$S2(i,j,L) = S1(i,j,L) * (1 + G_{ij}(L)) \qquad (12)$$

As seen from the equation (12), the second revised X-ray absorption characteristic S2(i, j, L) is obtained by making S1(i, j, L) closer to the actually measured value by correction of the distribution of the errors of S1(i, j, L) for the L direction for every X-ray detection element. Therefore, S2(i, j, L) correctly reflects characteristic variation of each X-ray detection element, and in addition, has many sample points $L=L_u$ (u=1 to U) for the L direction.

[Step S108]

Then, the BH correction function A is calculated in accordance with the equation (13) similar to the equation (5).

[Equation 13]

$$T(i,j,L) = A(S2(i,j,L)) \qquad (13)$$

In this case, the BH correction coefficient $a_k$(i, j) (k=1 to K) in the equation (1) is calculated by using the least square method. Further, the target value T(i, j, L) of the X-ray absorption characteristic is read out from the table TBL2.

[Step S109]

Finally, the calculated BH correction coefficients $a_k$(i, j) (k=1 to K) are saved in the table TBL1 (Step S109).

As described above, a series of the calculations of Steps S101 to S109 are repeatedly performed for H kinds of the imaging conditions, and such data of the BH correction coefficients as shown in FIG. 4 are finally saved.

<Calculation Method of Data for Correction Saved in Table TBL2>

Hereafter, there will be explained the calculation methods of the simulation value S(i, j, L) of the X-ray absorption characteristic and the target value T(i, j, L) of the X-ray absorption characteristic used for the calculation of the BH correction coefficients mentioned above.

Figure 13:
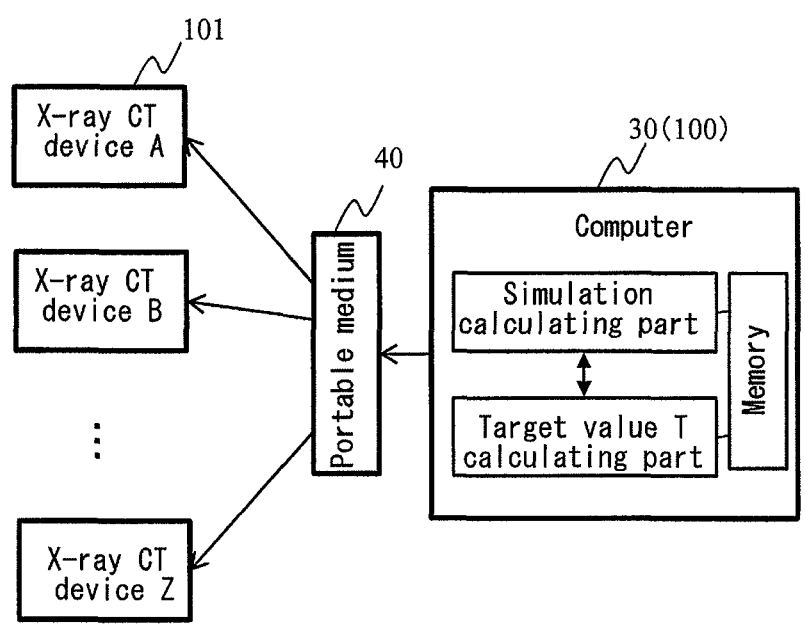
FIG. 13 shows outline of a calculation device or an operation part of an X-ray CT device for calculating data for correction saved in the table TBL2.

For these calculations, the correction part (the first operation part 21) of the X-ray CT device shown in FIG. 1 may have the function therefor, or they may be performed by using a computer 30 independent from the X-ray CT device as shown in FIG. 13. In the former case, it is not necessary to calculate these data in every maintenance measurement, and those calculated in advance can be saved in the table TBL2. Further, since the same values of TBL2 can be commonly used for X-ray CT devices of the same specification, it is not necessary to calculate them for each of such X-ray CT devices of the same specification.

When the calculations are performed with an independent computer 30 or a representative X-ray CT device 100, tables of the data obtained by the calculation may be stored in a portable medium 40 such as ROM, and the portable medium may be connected to each of X-ray CT devices A to Z 101, or the correction part of each of the X-ray CT devices 101 can read the data of the tables by using a known data transmission means.

The function of the computer or X-ray CT device for performing the aforementioned calculations is attained by a simulation calculation means, an X-ray absorption characteristic target value calculation means, and a memory means storing parameters used for these calculations, as shown in FIG. 13.

<<Calculation of Simulation Value>>

The calculation method of the simulation value $S(i, j, L)$ of the X-ray absorption characteristic will be explained first. As the simulation method of the physical process of X-ray, the ray-trace method, Monte Carlo method, and so forth are well known, and any of known simulation methods including these may be employed in the present invention. A calculation method using the ray-trace method will be explained hereafter as an example.

Figure 14:
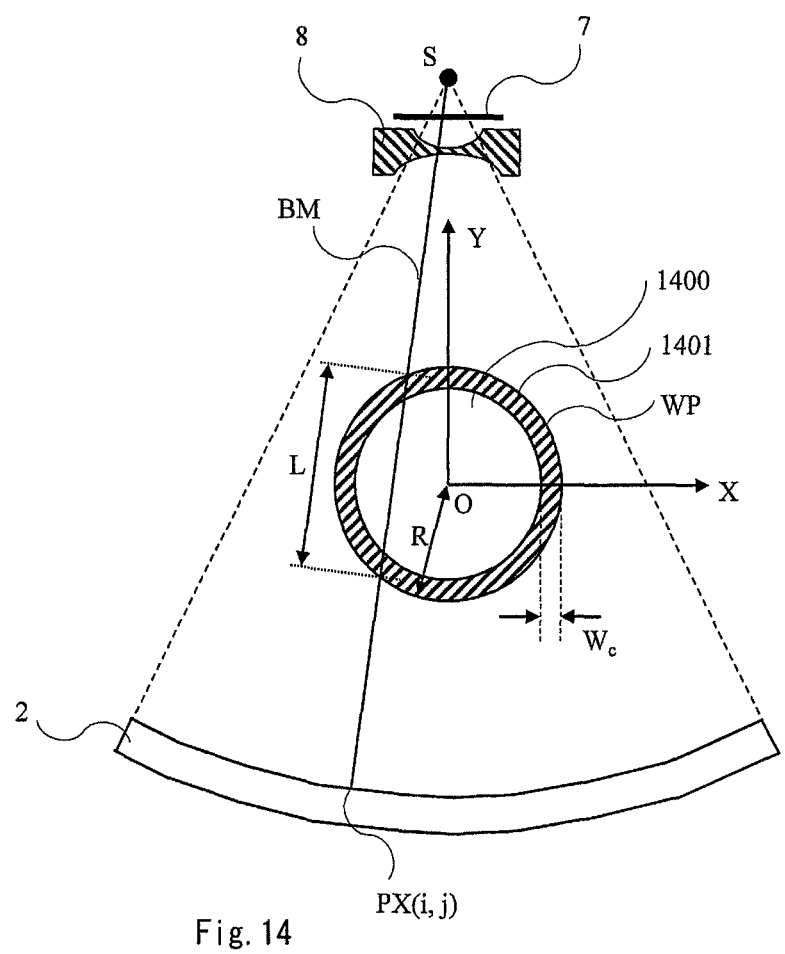
FIG. 14 is a drawing for explaining a method for calculating data for correction saved in the table TBL2 (simulation value S of X-ray absorption characteristic, and target value T of X-ray absorption characteristic).

$S(i, j, L)$ corresponds to projection data for an X-ray beam BM connecting an X-ray generation point S and an X-ray detection element $PX(i, j)$ as shown in FIG. 14, and for the calculation thereof, the influence of the BH effect at the time of the transmission of the X-ray through the radiation quality filter 7, the bow tie filter 8, and the water phantom (water phantom consisting of a container filled with water) WP are taken into consideration. In order to calculate projection data defined by the equation (2), imaging data $I(i, j, L)$ for the case of disposing the water phantom WP and air imaging data $I(i, j, 0)$ for the case of not disposing the water phantom WP are calculated first. The imaging data $I(i, j, L)$ are calculated in accordance with, for example, the following equation (14).

[Equation 14]

$$I(i, j, l) = \int_\varepsilon E(\varepsilon) e^{-\mu_f(\varepsilon)L_f} e^{-\mu_b(\varepsilon)L_b} e^{-\mu_c(\varepsilon)L_c} e^{-\mu_w(\varepsilon)L_w} \varepsilon d\varepsilon \quad (14)$$

In the equation (14), $\varepsilon$ represents energy of an X-ray, $E(\varepsilon)$ represents an energy spectrum of the X-ray radiated from the X-ray generation point S, $\mu_f(\varepsilon)$, $\mu_b(\varepsilon)$, $\mu_c(\varepsilon)$, and $\mu_w(\varepsilon)$ represent X-ray absorption coefficients of the radiation quality filter 7, the bow tie filter 8, the container 1401 of the water phantom WP, and water 1400, respectively. Further, $L_f$, $L_b$, $L_c$, and $L_w$ are total values of transmission path lengths of the X-ray beam BM in the radiation quality filter 7, the bow tie filter 8, the container 1401, and the water 1400, respectively. The transmission path length of the X-ray beam BM in the water phantom WP is $L=L_c+L_w$.

The air imaging data $I(i, j, 0)$ are calculated by substituting 0 for $L_c$ and $L_w$ ($L_c=L_w=0$) in the aforementioned equation (14).

Then, reference corrections of $I(i, j, L)$ and $I(i, j, 0)$ are carried out by using an equation similar to the equation (2) to calculate reference correction values $I_{cor}(i, j, L)$ and $I_{cor}(i, j, 0)$.

Finally, simulation-calculated values of the projection data corrected by the air correction are calculated in accordance with the definitional equation shown as the equation (3) (equation (15)).

[Equation 15]

$$S(i,j,L)=-\ln(I_{cor}(i,j,L)/I_{cor}(i,j,0)) \quad (15)$$

By the above procedure, $S(i, j, L)$ is calculated for all the combinations of X-ray detection elements $PX(i, j)$ and the values of L ($L_1$ to $L_U$).

It is noted that, since the transmission path length L is given in advance at the time of calculating the transmission data $I(i, j, L)$ for each of different transmission path lengths L, a water phantom WP having a transmission path length L and a radius R is virtually created on a computer. The center position of the water phantom WP corresponds to the rotation center O of the turntable 3, and therefore the value of the aforementioned radius R can be geometrically calculated. Further, thickness $W_c$ of the container 1401 is considered to be the same as the thickness of a real water phantom used for obtaining actually measured projection data in the maintenance measurement mode. As the real water phantom, those having a constant thickness $W_c$ of the container are used for all of N kinds of the water phantoms. Further, also for the water phantom WP virtually created on a computer and having an arbitrary radius R, the thickness of the containers is fixed to the same constant value as $W_c$ mentioned above. However, when the radius R becomes smaller than $2W_c$, $W_c$ is changed so as to be 0.5R ($W_c=0.5R$).

Further, $S(i, j, L)$ is calculated for each of a plurality of combinations of different tube voltages (energy of X-ray), radiation quality filters, and bow tie filters, which are the imaging conditions. The values of $S(i, j, L)$ calculated as described above are saved in such tables TBL2B-1 to TBL2B-H as shown in FIG. 8.

<<Calculation of Target Value T of X-Ray Absorption Characteristic>>

Hereafter, the calculation method of the target value $T(i, j, L)$ of the X-ray absorption characteristic will be explained. $T(i, j, L)$ corresponds to projection data of an X-ray beam BM connecting the X-ray generation point S and the X-ray detection element $PX(i, j)$ shown in FIG. 14, and are projection data not influenced by the BH effect obtained by assuming that the X-ray is a monochromatic X-ray. The target value T of the X-ray absorption characteristic is also calculated for a plurality of imaging conditions consisting of combinations of different imaging parameters, like S mentioned above.

When the phantom consists of 100% water, the value of $T(i, j, L)$ can be calculated by using the equation of $T(i, j, L)=\mu_w L_w$ (in the equation, $\mu_w$ is X-ray absorption coefficient of water for a monochromatic X-ray, and $L_w$ is an X-ray transmission path length of the X-ray beam BM in the water phantom). However, actually usable water phantom consists of water filled in a container, and the value of $T(i, j, L)$ is calculated in accordance with the equation (16).

[Equation 16]

$$T(i,j,L)=\mu_w(\alpha L_c+L_w) \quad (16)$$

In the equation, $\mu_c$ is X-ray absorption coefficient of the container for a monochromatic X-ray, and $\alpha$ is $\mu_c/\mu_w$ ($\alpha=\mu_c/\mu_w$). $L_c$ is the X-ray transmission path length of the X-ray beam BM in the container. For the normalization of the CT value, $\mu_w$ is set to be 1000 ($\mu_w=1000$).

The value of $\alpha$ is a substantial ratio of the X-ray absorption coefficient of the container and the X-ray absorption coefficient of water, and is derived by using actually measured data or by simulation calculation. Since the value of $\alpha$ differs for every imaging condition, it is derived for each of H kinds of the imaging conditions.

Hereafter, there will be explained the method for deriving the ratio of the X-ray absorption coefficient of the container and the X-ray absorption coefficient of water, $\alpha=\mu_c/\mu_w$, by using actually measured data.

Figure 15:
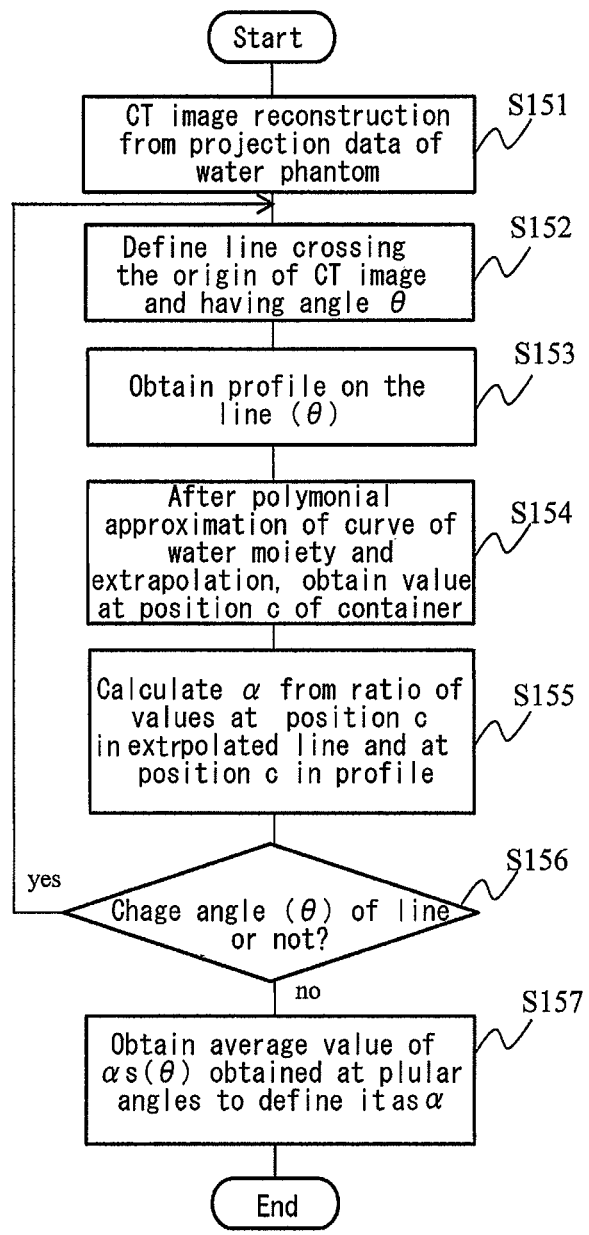
FIG. 15 is a flowchart showing a part of calculation procedure for obtaining the target value T of X-ray absorption characteristic.
Figure 16:
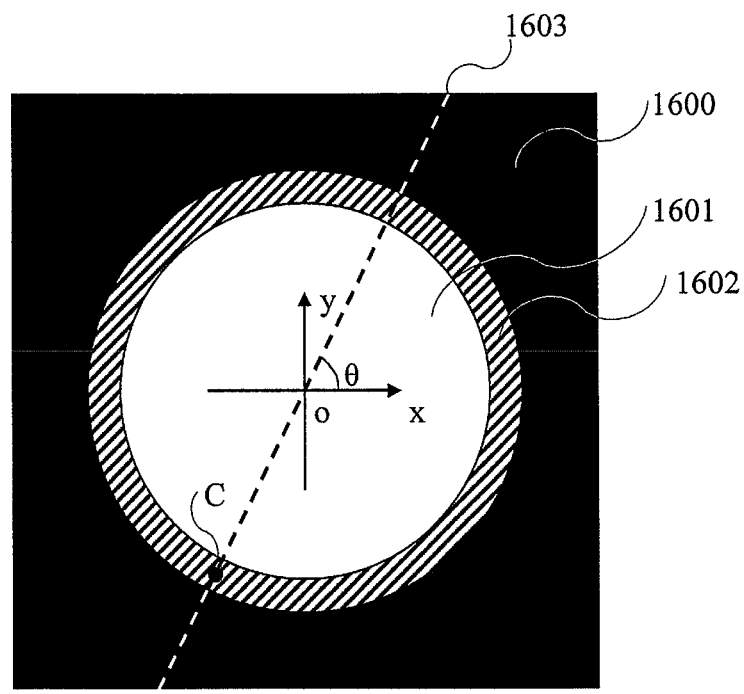
FIG. 16 is a schematic drawing of a CT image reconstructed on the basis of imaging data of a water phantom WP.

The procedure is shown in FIG. 15. The water phantom WP consisting of a container filled with water is imaged first, and a CT image is reconstructed without carrying out the BH correction (Step S151). The procedure of this image reconstruction is the same as the procedure shown in FIG. 3 except for the BH correction. A schematic drawing of a CT image reconstructed on the basis of imaging data of the water phantom WP is shown in FIG. 16. As shown in FIG. 16, the CT image of the water phantom WP consists of an air moiety 1600, a water moiety 1601, and a container moiety 1602.

Figure 17:
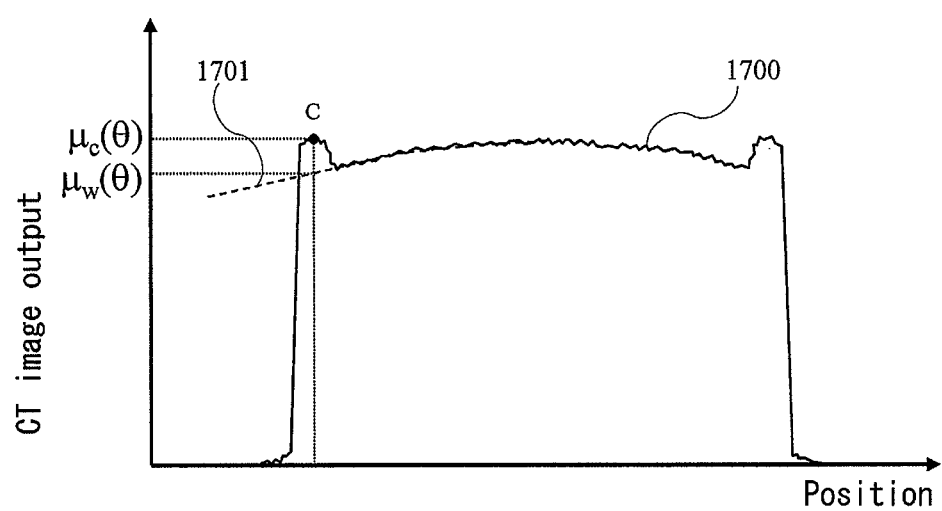
FIG. 17 shows a profile of a CT image on the straight line 1603 shown in FIG. 16.

Then, in the CT image, a straight line 1603 passing through the center O of the water phantom (cylinder) is defined, and a profile of the CT image on the straight line 1603 is obtained (Steps S152 and S153). An example of profile 1700 is shown in FIG. 17. Since this reconstructed image is obtained without the BH correction, the profile 1700 has a curved shape for the water moiety as shown in the drawing.

The curve 1701 of the water moiety is approximated with a polynomial or the like, and a curve 1700 corresponding to the container moiety (1602 in FIG. 16) is obtained by extrapolation (Step S154). This curve 1701 is a profile expected for the case where it is assumed that the container of the water phantom WP is constituted with water. It can be considered that the value of the curve 1701 at the position C corresponding to the center position c of the container moiety 1602 on the straight line 1603 is approximately the X-ray absorption coefficient $\mu_w(\theta)$ of the water at this position c. $\theta$ is an angle between the straight line 1603 and the coordinate axis X of the CT image. Further, it can be considered that the value of the profile 1700 at the position C is approximately the X-ray absorption coefficient $\mu_c(\theta)$ of the container. Therefore, the ratio $\alpha(\theta)$ ($=\mu_c(\theta)/\mu_w(\theta)$) can be calculated by using these $\mu_w(\theta)$ and $\mu_c(\theta)$ (Step S155).

Signals represented by the profile 1700 include random noise components resulting from quantum noises of X-ray, circuit noises of the X-ray detector 2, and so forth. In order to prevent degradation of accuracy of measured value of a resulting from these noise components, it is preferable to calculate $\alpha(\theta)$ for various angles $\theta$ (0 to 360 degrees) by changing the angle $\theta$ of the straight line 1603 passing the starting point o, and use the average as the value of $\alpha$ (Steps S156 and S157).

Hereafter, the method for calculating $\alpha$ by using a simulation value will be explained. In this method, $\alpha$ is also obtained from a reconstructed CT image, but the CT image is reconstructed by using simulation projection data created in order to calculate a simulation calculated value S, not projection data obtained by actual measurement of CT image (not corrected by the BH correction). The simulation projection data are obtained by such simulation calculation performed in consideration of the BH effect as explained with reference to FIG. 14, and the same profile as that of FIG. 17 can be obtained. As the case of using a CT image reconstructed from actually measured projection data, the X-ray absorption coefficient $\mu_w$ of water at the container moiety (position c) is calculated by approximation of the curve of the water moiety of this profile and extrapolation using it, and $\alpha$ is calculated from the calculated $\mu_w$ and the X-ray absorption coefficient $\mu_c$ of the container.

However, when simulation projection data are used, the CT image does not contain quantum noises of X-ray or circuit noises, and therefore it is not necessary to calculate $\alpha(\theta)$ for various angles $\theta$ for noise reduction. Accordingly, for example, $\alpha(0)$ may be calculated as the value of $\alpha$, and therefore there is obtained an advantage that the value of $\alpha$ can be quickly calculated.

The method for calculating T(i, j, L) on the basis of the value of $\alpha$ in accordance with the equation (16) is explained above. Hereafter, another method for calculating T(i, j, L) without using $\alpha$ will be explained.

Figure 18:
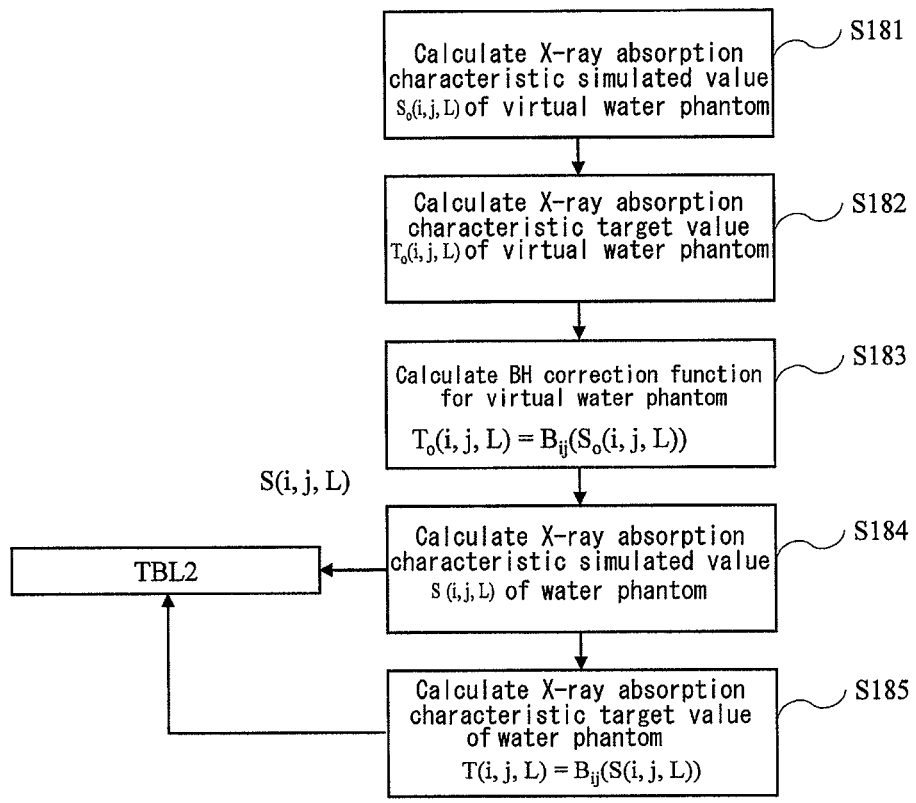
FIG. 18 is a flowchart for explaining another example of the calculation method of the target value T of X-ray absorption characteristic.

The procedure of this method is shown in FIG. 18. First, a virtual water phantom corresponding to the water phantom WP shown in FIG. 14 in which the thickness of the containers is 0 ($W_c$=0) is created on a computer, and a simulation value $S_o$(i, j, L) of the X-ray absorption characteristic for the virtual water phantom is calculated (Step S181). Such calculation can be easily realized by substituting 0 for $L_c$ ($L_c$=0) in the equation (14).

Then, a target value $T_o$(i, j, L) of the X-ray absorption characteristic is calculated for the virtual water phantom (Step S182). The value of $T_o$(i, j, L) is calculated by substituting 0 for $L_c$ ($L_c$=0) in the equation (16). Since the member of $\alpha$ is eliminated from the equation (16) by such substitution, the value of $T_o$(i, j, L) can be easily calculated without deriving the value of $\alpha$.

Then, the BH correction function $B_{ij}$ is calculated for the virtual water phantom by using an equation similar to the equation (13) [$T_o$(i, j, L)=$B_{ij}$($S_o$(i, j, L))] (Step S183). The BH correction coefficients $b_k$(i, j) (k=1 to K) of this correction function $B_{ij}$ are calculated by using the least square method. These BH correction coefficients are data having the same structure as that of such BH correction coefficients used in the main measurement mode as shown in FIG. 4, and they are saved in the table TBL3 of a computer that performs this calculation (when the calculation is performed by the X-ray CT device, they are saved in, for example, the table TBL1).

Then, a water phantom WP contained in a container having a thickness (Wc≠0) is supposed, and the simulation value S(i, j, L) of the X-ray absorption characteristic is calculated for this water phantom WP (Step S184). The calculation method of the simulation value S(i, j, L) is the same as that already explained above with reference to FIG. 14.

Finally, the calculated simulation value S(i, j, L) is subjected to the BH correction by using the BH correction coefficients calculated in Step S183 in accordance with the equation T(i, j, L)=$B_{ij}$(S(i, j, L)) to obtain data corrected by the BH correction. The relation between the simulation value S and the corrected data is the same as the relation between the X-ray absorption characteristic S before the correction and the target value T of the X-ray absorption characteristic shown in FIG. 7, and this value is used as the target value T(i, j, L) of the X-ray absorption characteristic (Step S185).

According to the method for calculating the target value T explained above, the BH correction derived for a virtual water phantom of which thickness of container is 0, which can hardly be actually produced, is performed for the X-ray absorption characteristic S(i, j, L) calculated for a realistic water phantom of which thickness of container is not 0 to calculate T(i, j, L), and it does not require the value of $\alpha$ for the calculation. Therefore, it does not require operation for reconstructing a CT image of a water phantom for deriving the value of $\alpha$ ($=\mu_c/\mu_w$), and has an advantage that the value of T(i, j, L) can be quickly calculated.

The target value T(i, j, L) of the X-ray absorption characteristic is calculated for each of a plurality of combinations of different tube voltages (energy of X-ray), radiation quality filters, and bow tie filters, which are the imaging conditions. The values of T(i, j, L) calculated as described above are saved in such tables TBL2B-1 to TBL2B-H as shown in FIG. 8.

<Effect of BH Correction>

Figure 19:
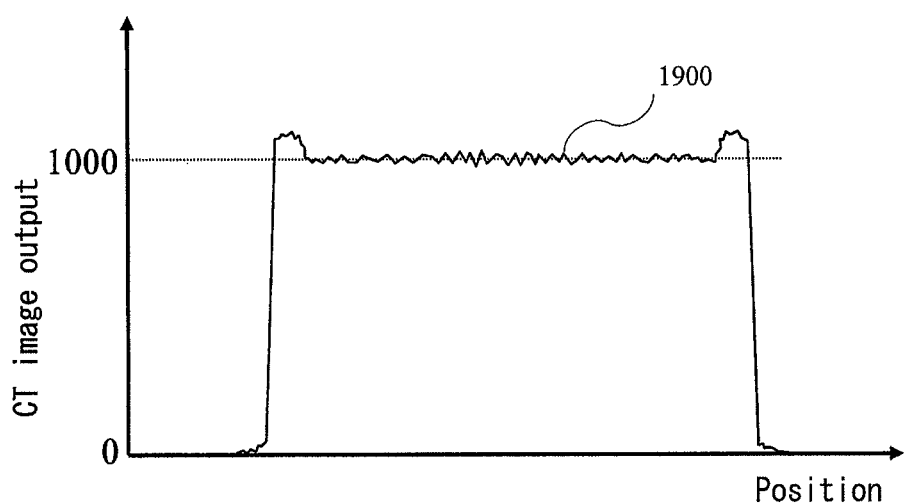
FIG. 19 shows a profile of a CT image of a water phantom reconstructed on the basis of projection data corrected by the BH correction in an X-ray CT device according to an embodiment of the present invention.
Figure 20:
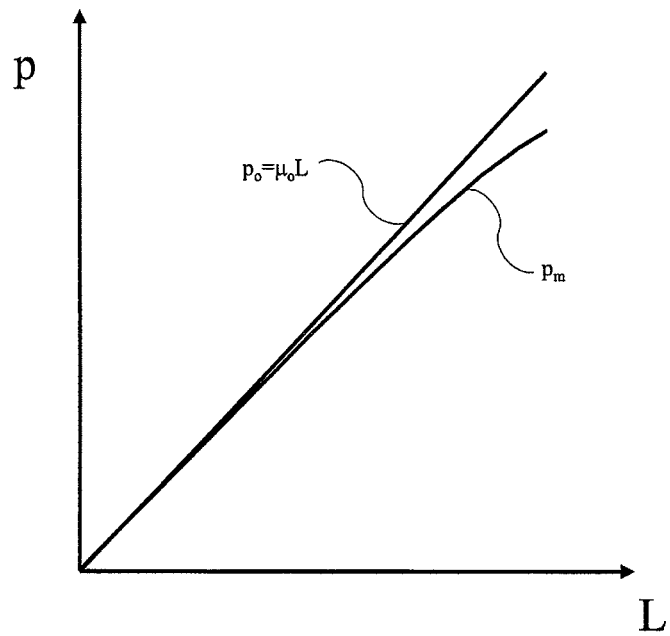
FIG. 20 shows relation between X-ray transmission path length L of an X-ray passing through a subject consisting of a uniform material and having uniform density and projection data p.
Figure 21:
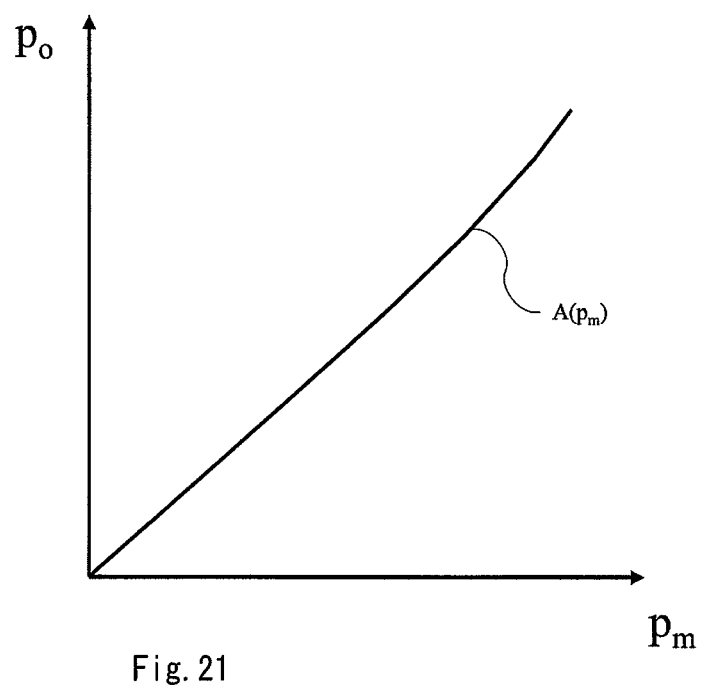
FIG. 21 shows relation between projection data $p_m$ for a polychromatic X-ray and projection data $p_o$ for a monochromatic X-ray.

A profile 1900 of a CT image of the water phantom reconstructed on the basis of projection data corrected by the BH correction is shown in FIG. 19. This profile shall also be on the straight line 1603 shown in FIG. 16. It can be seen that, compared with the profile 1700 obtained without carrying out the BH correction shown in FIG. 17, the profile 1900 obtained with carrying out the BH correction shows more uniform CT image output of the water moiety, in which the CT image output is about 1000. This image output value is a value before the conversion into CT value, and a final CT image is outputted with values uniformly smaller by 1000 than this image output value. As described above, the CT values of the water moiety can be equalized by performing the BH correction, and the effect of the aforementioned equalization can also be obtained in a CT image of the human body most of which consists of water. Incorrect diagnosis resulting from inhomogeneity of the CT value can be thereby reduced, and the diagnostic ability can be thereby improved with improvement of quantitative determination ability for the CT value.

As described above, with the X-ray CT device of this embodiment, projection data can be highly accurately approximated with those obtained with a small number of actual measurements on the basis of simulation calculation results in the maintenance measurement for obtaining basic data required for the BH correction. Since numbers of the kinds of the phantoms to be measured can be thereby reduced while maintaining high BH correction accuracy and number of the measurement, it is effective for reducing the production cost of the phantoms and the operation cost of the measurement. Further, since it is not necessary to use any phantoms other than water phantom, such as polyethylene phantom, there can be obtained an effect that the BH correction and normalization of CT value can be achieved by a common measurement to further reduce the production cost of the phantom and the operation cost of the measurement. Furthermore, as the values of TBL2 required for the calculation of the BH correction coefficients, those calculated in advance can be used, and can be commonly used for X-ray CT devices of the same specification. Therefore, it has an effect that it is not necessary to perform the complicated calculations such as simulation calculation and reconstruction operation of CT image for every maintenance measurement, and the BH correction coefficients can be quickly calculated.

Although an embodiment of the X-ray CT device of the present invention has been explained above, the present invention is of course not limited to this example, and can be variously changed without departing from the scope of the present invention. For example, in the above example of the invention, there is explained a method of improving the BH correction accuracy on the basis of X-ray simulation calculation results with a small number of imaging data samples of water phantoms. However, the same effect of reducing the number of phantoms and the operation amount can also be obtained even when the aforementioned method is applied to imaging data of phantoms formed with another material such as polyethylene.

Further, in the above embodiment of the present invention, the position of the center axis of the water phantom WP is substantially the same as the position of the rotation axis of the turntable 3. However, the position may be intentionally deviated. In such a case, samples of imaging data can be obtained for a plurality of the path lengths L with the rotation of the rotational imaging system, and therefore there is expected an effect that the BH correction accuracy can be further improved.

Furthermore, in the above embodiment of the present invention, there has been mentioned a method of using ray-trace simulation for the simulation calculation of the X-ray absorption characteristic $S(i, j, L)$. However, other known simulation methods such as Monte Carlo simulation may also be used. Further, when the ray-trace simulation is used, the calculation method is not limited to the method of using the equation (14). For example, it is also of course possible to improve the simulation accuracy by introducing an X-ray detection process with an X-ray detection element or the like, or conversely, improve the simulation speed by skipping a part of the calculation process.

Further, in the above embodiment of the present invention, the data for the BH correction are calculated by a function of the operation part of the X-ray CT device. However, the function of the operation part can be provided in a calculation device independent from the X-ray CT device.

That is, such a calculation device is a calculation device for calculating data for the BH correction to be used for the beam hardening correction in an X-ray CT device, and comprises a first calculation part for calculating projection data including influence of the beam hardening effect for a plurality of kinds of virtual phantoms consisting of water phantoms constituted with containers filled with water and providing different beam path lengths under a plurality of kinds of imaging conditions by simulation, and calculating simulation calculation values S of X-ray absorption characteristic indicating relation between beam path length and projection data, and a second calculation part for calculating target values T of the X-ray absorption characteristic not including the beam hardening effect for a plurality of kinds of the virtual phantoms, and the second calculation part comprises an image reconstruction means for reconstructing a CT image by using projection data calculated by simulation for a virtual subject or projection data actually measured for a subject equivalent to the virtual subject, calculates ratios ($\alpha$) of X-ray absorption coefficients of the containers of the virtual phantoms and water from profile of the CT image, and calculates the target values T of the X-ray absorption characteristic by using the ratios.

Alternatively, the calculation device is a calculation device for calculating data for the BH correction to be used for the beam hardening correction in an X-ray CT device, and comprises a first calculation part for calculating projection data including influence of the beam hardening effect for a plurality of kinds of virtual phantoms consisting of water phantoms constituted with containers filled with water and providing different beam path lengths under a plurality of kinds of imaging conditions by simulation, and calculating simulation calculation values S of X-ray absorption characteristic indicating relation between beam path length and projection data, a second calculation part for calculating target values T of the X-ray absorption characteristic not including the beam hardening effect for a plurality of kinds of the virtual phantoms, and a third calculation part for calculating a BH correction function by using the simulation-calculated values S calculated by the first calculation part with assuming that thickness of the containers of the virtual phantoms is 0 and the target values T calculated by the second calculation part with assuming that thickness of the containers of the virtual phantoms is 0, and the second calculation part applies the BH correction function calculated by the third calculation part to the simulation-calculated values S calculated by the first calculation part for the virtual phantoms in which thickness of the containers is variously changed to calculate simulation values corrected by the BH correction as the target values T of the X-ray absorption characteristic.

Further, the data for the BH correction created by the operation part of the X-ray CT device or the aforementioned calculation device can be saved in a general-purpose recording medium and commonly used in X-ray CT devices of the same specification.

That is, the recording medium for X-ray CT devices of the present invention is a recording medium for X-ray CT devices saving data for BH correction to be used for the beam hardening correction in an X-ray CT device, and the data for BH correction is created by the operation part of the X-ray CT device or the aforementioned calculation device, and consist of simulation-calculated values S of X-ray absorption characteristic including the influence of the beam hardening effect and target values T of the X-ray absorption characteristic not including influence of the beam hardening effect for a plurality of kinds of virtual phantoms providing different X-ray transmission path lengths.

In this recording medium for X-ray CT devices, the data for BH correction may further contain X-ray transmission path lengths of water moieties calculated for a plurality of kinds of the virtual phantoms.

Further, the operation of the X-ray CT device mentioned above in the maintenance measurement mode can be performed independently from the imaging and the BH correction performed by the X-ray CT device.

That is, the method for maintaining an X-ray CT device of the present invention comprises the step of performing imaging of a plurality of kinds of phantoms under a plurality of kinds of imaging conditions to obtain actually measured values of X-ray absorption characteristic of a plurality of kinds of the phantoms, the step of inputting simulation-calculated values of the X-ray absorption characteristics obtained beforehand by simulation for virtual phantoms equivalent to a plurality of kinds of the phantoms to calculate errors between the simulation-calculated values and the actually measured values, the step of revising the simulation-calculated values by using the errors, the step of inputting target values of X-ray absorption characteristics calculated beforehand and calculating BH correction coefficients using the target values and the revised simulation-calculated values of the X-ray absorption characteristic, and the step of saving the calculated BH correction coefficients as a table.

In the aforementioned maintenance method, the step of calculating the errors may comprise a first error calculation step of calculating the errors for every sequence of the X-ray detection elements constituting the X-ray detector for the simulation-calculated values, and a second error calculation step of calculating the errors for every X-ray detection element constituting the X-ray detector.

INDUSTRIAL APPLICABILITY

According to the present invention, the accuracy of the BH correction can be improved in an X-ray CT device for medical use, and reduction of incorrect diagnosis resulting from inhomogeneity of the CT values and improvement in the diagnostic ability based on improvement in quantitative determination ability for the CT values can be thereby realized. Further, the operation cost can be reduced by reducing the number of measurements in the maintenance measurement required for acquisition of the basic data for the BH correction.

DESCRIPTION OF NUMERAL NOTATIONS

1 . . . X-ray tube
2 . . . X-ray detector
3 . . . Turntable
4 . . . Top of bed
5 . . . Gantry
6 . . . Opening
7 . . . Radiation quality filter
8 . . . Bow tie filter
9 . . . Collimator
11 . . . Operation console
12 . . . Imaging controller
21 . . . First operation part (correction part)
22 . . . Second operation part (image reconstruction part)
23 . . . Memory (MEM1)
24 . . . Memory (MEM2)
TBL1 . . . Table
TBL2 . . . Table
SB . . . Subject
WP . . . Water phantom

The invention claimed is:

1. An X-ray CT device comprising an X-ray generation part, an X-ray detection part oppositely disposed to the X-ray generation part and having a plurality of X-ray detection elements, a correction part for correcting data detected by the X-ray detection part, and an image reconstruction part for reconstructing a CT image by using corrected data, wherein:

the correction part comprises a beam hardening correction part for correcting the detected data on the basis of a BH correction function representing relation between target values of X-ray absorption characteristic of a predetermined subject and X-ray absorption characteristic of the predetermined subject under the influence of beam hardening, and the beam hardening correction part comprises:

an X-ray absorption characteristic calculation part for calculating X-ray absorption characteristic by using errors between simulation-calculated values of X-ray absorption characteristic obtained beforehand for a virtual phantom by simulation and actually measured values of X-ray absorption characteristic of a phantom equivalent to the virtual phantom, and a BH correction function calculation part for calculating the BH correction function by using the X-ray absorption characteristic calculated by the X-ray absorption characteristic calculation part and target values of X-ray absorption characteristic calculated beforehand, and corrects data measured for a test subject on the basis of the BH correction function calculated by the BH correction function calculation part.

2. The X-ray CT device according to claim 1, wherein:
the correction part comprises an air correction part for carrying out air correction of the data detected by the X-ray detection part, and the actually measured data used in the BH correction function calculation part are actually measured data corrected by the air correction in the air correction part.

3. The X-ray CT device according to claim 1, wherein:
the X-ray absorption characteristic calculation part comprises a first revision part for calculating errors of the simulation-calculated values of the X-ray absorption characteristic and the actually measured values of the X-ray absorption characteristic, and revising the simulation-calculated values by using the errors, and a second revision part for calculating errors of the simulation-calculated values revised by the first revision part and the actually measured values of the X-ray absorption characteristic, and further revising the revised simulation-calculated values by using the errors, and the simulation-calculated values revised by the second revision part are used as the X-ray absorption characteristic.

4. The X-ray CT device according to claim 1, which further comprises:
a first table saving simulation-calculated values of the X-ray absorption characteristic and target values of the X-ray absorption characteristic, and a second table saving a BH correction function calculated by the BH correction function calculation part.

5. The X-ray CT device according to claim 1, wherein:
the virtual phantom and the phantom consist of water filled in a container.

6. The X-ray CT device according to claim 1, which further comprises a part for calculating data for correction for calculating simulation-calculated values of the X-ray absorption characteristic and target values of the X-ray absorption characteristic.

7. The X-ray CT device according to claim 6, wherein:
the part for calculating data for correction comprises
a first calculation part for calculating projection data including influence of the beam hardening effect for a plurality of kinds of virtual phantoms consisting of water phantoms constituted with containers filled with water and providing different beam path lengths under a plurality of kinds of imaging conditions by simulation, and calculating simulation calculation values S of X-ray absorption characteristic indicating relation between the beam path length and projection data, and
a second calculation part for calculating ratios ($\alpha$) of X-ray absorption coefficients of the containers of the virtual phantoms and water from profile of a CT image reconstructed by using projection data calculated by simulation for the virtual subject or projection data actually measured for a subject equivalent to the virtual subject, and calculating target values T of the X-ray absorption characteristic by using the ratios.

8. The X-ray CT device according to claim 6, wherein:
the part for calculating data for correction comprises
a first calculation part for calculating projection data including influence of the beam hardening effect for a plurality of kinds of virtual phantoms consisting of water phantoms constituted with containers filled with water and providing different beam path lengths under a plurality of kinds of imaging conditions by simulation, and calculating simulation calculation values S of X-ray absorption characteristic indicating relation between the beam path length and projection data,
a second calculation part for calculating target values T of the X-ray absorption characteristic not including the beam hardening effect for a plurality of kinds of the virtual phantoms, and
a third calculation part for calculating a BH correction function from the simulation-calculated values S calculated by the first calculation part with assuming that thickness of the containers of the virtual phantoms is 0 and the target values T calculated by the second calculation part with assuming that thickness of the containers of the virtual phantoms is 0, and
the second calculation part applies the BH correction function calculated by the third calculation part to the simulation-calculated values S calculated by the first calculation part for the virtual phantoms in which thickness of the containers is variously changed to calculate simulation values corrected by the BH correction as the target values T of the X-ray absorption characteristic.

9. An X-ray CT device comprising a calculation device for calculating data for BH correction to be used for the beam hardening correction in the X-ray CT device, including:
a first calculation part for calculating projection data including influence of the beam hardening effect for a plurality of kinds of virtual phantoms consisting of water phantoms constituted with containers filled with water and providing different beam path lengths under a plurality of kinds of imaging conditions by simulation, and calculating simulation calculation values S of X-ray absorption characteristic indicating relation between the beam path length and projection data, and
a second calculation part for calculating target values T of the X-ray absorption characteristic not including the beam hardening effect for a plurality of kinds of the virtual phantoms, and
the second calculation part comprises an image reconstruction means for reconstructing a CT image by using projection data calculated by simulation for a virtual subject or projection data actually measured for a subject equivalent to the virtual subject,
calculates ratios ($\alpha$) of X-ray absorption coefficients of the containers of the virtual phantoms and water from profile of the CT image, and calculates the target values T of the X-ray absorption characteristic by using the ratios.

10. An X-ray CT device comprising a calculation device for calculating data for BH correction to be used for the beam hardening correction in the X-ray CT device, including:
a first calculation part for calculating projection data including influence of the beam hardening effect for a plurality of kinds of virtual phantoms consisting of water phantoms constituted with containers filled with water and providing different beam path lengths under a plurality of kinds of imaging conditions by simulation, and calculating simulation calculation values S of X-ray absorption characteristic indicating relation between the beam path length and projection data, and
a second calculation part for calculating target values T of the X-ray absorption characteristic not including the beam hardening effect for a plurality of kinds of the virtual phantoms, and
a third calculation part for calculating a BH correction function from the simulation-calculated values S calculated by the first calculation part with assuming that thickness of the containers of the virtual phantoms is 0 and the target values T calculated by the second calculation part with assuming that thickness of the containers of the virtual phantoms is 0, and
the second calculation part applies the BH correction function calculated by the third calculation part to the simulation-calculated values S calculated by the first calculation part for the virtual phantoms in which thickness of the containers is variously changed to calculate simulation values corrected by the BH correction as the target values T of the X-ray absorption characteristic.

11. A non-transitory computer-readable medium storing executable instructions that, in response to execution, cause an X-ray CT device to perform operations comprising:
   saving data for beam hardening (BH) correction to be used for beam hardening correction in the X-ray CT device, wherein the data for BH correction includes simulation-calculated values S of X-ray absorption characteristic including the influence of the beam hardening effect and target values T of X-ray absorption characteristic not including the influence of the beam hardening effect for a plurality of kinds of virtual phantoms providing different X-ray transmission path lengths,
   calculating the values by the calculation device,
   calculating, by a first calculation part, projection data including influence of the beam hardening effect for a plurality of kinds of virtual phantoms consisting of water phantoms constituted with containers filled with water and providing different beam path lengths under a plurality of kinds of imaging conditions by simulation, and calculating simulation calculation values S of X-ray absorption characteristic indicating relation between the beam path length and projection data, and
   calculating, by a second calculation part, target values T of the X-ray absorption characteristic not including the beam hardening effect for a plurality of kinds of the virtual phantoms,
   reconstructing, by an image reconstruction part of the second calculation part, a CT image by using projection data calculated by simulation for a virtual subject or projection data actually measured for a subject equivalent to the virtual subject, calculating ratios ($\alpha$) of X-ray absorption coefficients of the containers of the virtual phantoms and water from profile of the CT image, and calculating the target values T of the X-ray absorption characteristic by using the ratios.

12. The non-transitory computer-readable medium according to claim 11, wherein:
   the data for BH correction further comprise X-ray transmission path lengths of water moieties calculated for a plurality of kinds of the virtual phantoms.

13. A method for maintaining an X-ray CT device, comprising:
   performing imaging of a plurality of kinds of phantoms under a plurality of kinds of imaging conditions to obtain actually measured values of X-ray absorption characteristic for a plurality of kinds of the phantoms;
   inputting simulation-calculated values of the X-ray absorption characteristic obtained beforehand by simulation for virtual phantoms equivalent to a plurality of kinds of the phantoms to calculates errors between the simulated values and the actually measured values;
   revising the simulation-calculated values by using the errors;
   inputting target values of X-ray absorption characteristic calculated beforehand and calculating BH correction coefficients by using the target values and the revised simulation-calculated values of the X-ray absorption characteristic, and
   saving the calculated BH correction coefficients as a table.

14. The method for maintaining an X-ray CT device according to claim 13, wherein:
   the step of calculating the errors comprises a first error calculation step of calculating the errors for every sequence of the X-ray detection elements constituting the X-ray detector for the simulation-calculated values, and a second error calculation step of calculating the errors for every X-ray detection element constituting the X-ray detector.

15. An X-ray CT device comprising an imaging means having an X-ray tube, an X-ray detector oppositely disposed to the X-ray tube, and a turntable for rotating the X-ray tube and X-ray detector around a test subject, a control means for controlling operations of the imaging means, an operation part for processing signals detected by the X-ray detector to create a CT image of the test subject, and a table saving data for correction to be used by the operation part, wherein:
   the operation part comprises an air correction means for carrying out air correction of the signals detected by the X-ray detector, and a BH correction part for correcting the signals corrected by the air correction using a beam hardening correction coefficient,
   the table comprises, as the data for correction, a first table saving the beam hardening correction coefficients, and a second table saving simulation-calculated values of X-ray absorption characteristic obtained by simulation so as to include the beam hardening effect and indicating relation between X-ray transmission path length in a virtual phantom and projection data, and target values of the X-ray absorption characteristic calculated for the virtual phantom so as not to include the beam hardening effect, and
   the X-ray CT device further comprises a BH correction coefficient calculation part for calculating the BH correction coefficients by using the simulation-calculated values and target values of the X-ray absorption characteristic, and signals detected by the X-ray detector through imaging of a phantom equivalent to the virtual phantom, and saving the BH correction coefficients in the first table.

16. The X-ray CT device according to claim 15, wherein:
   the data saved in the second table are data for correction calculated by the calculation device including:
   a first calculation part that calculates projection data including influence of the beam hardening effect for a plurality of kinds of virtual phantoms consisting of water phantoms constituted with containers filled with water and providing different beam path lengths under a plurality of kinds of imaging conditions by simulation, and calculating simulation calculation values S of X-ray absorption characteristic indicating relation between the beam path length and projection data, and
   a second calculation part that calculates target values T of the X-ray absorption characteristic not including the beam hardening effect for a plurality of kinds of the virtual phantoms,
   wherein the second calculation part comprises an image reconstruction part that reconstructs a CT image by using projection data calculated by simulation for a virtual subject or projection data actually measured for a subject equivalent to the virtual subject, calculates ratios ($\alpha$) of X-ray absorption coefficients of the containers of the virtual phantoms and water from profile of the CT image, and calculates the target values T of the X-ray absorption characteristic by using the ratios.

17. A recording medium for X-ray CT devices saving data for BH correction to be used for the beam hardening correction in an X-ray CT device, wherein:
   the data for BH correction comprise simulation-calculated values S of X-ray absorption characteristic including the influence of the beam hardening effect and target values T of X-ray absorption characteristic not including the influence of the beam hardening effect for a plurality of kinds of virtual phantoms providing different X-ray transmission path lengths, wherein the values are calculated by the calculation device including:
- a first calculation part that calculates projection data including influence of the beam hardening effect for a plurality of kinds of virtual phantoms consisting of water phantoms constituted with containers filled with water and providing different beam path lengths under a plurality of kinds of imaging conditions by simulation, and calculating simulation calculation values S of X-ray absorption characteristic indicating relation between the beam path length and projection data, and
- a second calculation part that calculates target values T of the X-ray absorption characteristic not including the beam hardening effect for a plurality of kinds of the virtual phantoms, and
- a third calculation part that calculates a BH correction function from the simulation-calculated values S calculated by the first calculation part with assuming that thickness of the containers of the virtual phantoms is 0 and the target values T calculated by the second calculation part with assuming that thickness of the containers of the virtual phantoms is 0,
- wherein the second calculation part applies the BH correction function calculated by the third calculation part to the simulation-calculated values S calculated by the first calculation part for the virtual phantoms in which thickness of the containers is variously changed to calculate simulation values corrected by the BH correction as the target values T of the X-ray absorption characteristic.

18. The X-ray CT device according to claim 15, wherein:
the data saved in the second table are data for correction calculated by the calculation device including:
- a first calculation part that calculates projection data including influence of the beam hardening effect for a plurality of kinds of virtual phantoms consisting of water phantoms constituted with containers filled with water and providing different beam path lengths under a plurality of kinds of imaging conditions by simulation, and calculating simulation calculation values S of X-ray absorption characteristic indicating relation between the beam path length and projection data, and
- a second calculation part that calculates target values T of the X-ray absorption characteristic not including the beam hardening effect for a plurality of kinds of the virtual phantoms, and
- a third calculation part that calculates a BH correction function from the simulation-calculated values S calculated by the first calculation part with assuming that thickness of the containers of the virtual phantoms is 0 and the target values T calculated by the second calculation part with assuming that thickness of the containers of the virtual phantoms is 0,
- wherein the second calculation part applies the BH correction function calculated by the third calculation part to the simulation-calculated values S calculated by the first calculation part for the virtual phantoms in which thickness of the containers is variously changed to calculate simulation values corrected by the BH correction as the target values T of the X-ray absorption characteristic.

\* \* \* \* \*